(12) United States Patent
Zhan et al.

(10) Patent No.: US 11,490,874 B2
(45) Date of Patent: Nov. 8, 2022

(54) SELF CALIBRATION METHOD AND APPARATUS FOR CORRECTING OFFSET ANGLE IN A PHOTON COUNTING COMPUTED TOMOGRAPHY SYSTEM

(71) Applicant: CANON MEDICAL SYSTEMS CORPORATION, Otawara (JP)

(72) Inventors: Xiaohui Zhan, Vernon Hills, IL (US); Ilmar Hein, Vernon Hills, IL (US); Xiaofeng Niu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/206,873

(22) Filed: Mar. 19, 2021

(65) Prior Publication Data

US 2022/0296202 A1 Sep. 22, 2022

(51) Int. Cl.
*A61B 6/00* (2006.01)

(52) U.S. Cl.
CPC ............ *A61B 6/584* (2013.01); *A61B 6/4241* (2013.01); *A61B 6/585* (2013.01)

(58) Field of Classification Search
None
See application file for complete search history.

(56) References Cited

U.S. PATENT DOCUMENTS

| | | | | |
|---|---|---|---|---|
| 2007/0023713 A1* | 2/2007 | Bruder | ................... | A61B 6/583 250/505.1 |
| 2008/0273666 A1* | 11/2008 | Walter | ................... | A61B 6/505 378/185 |
| 2012/0093282 A1 | 4/2012 | Kappler | | |
| 2016/0171725 A1* | 6/2016 | Liu | ................... | G06T 11/005 378/207 |
| 2016/0239971 A1* | 8/2016 | Yu | ................... | G06T 11/005 |
| 2018/0197314 A1* | 7/2018 | De Man | ................... | G06T 11/006 |

FOREIGN PATENT DOCUMENTS

JP 2008-46021 A 2/2008

OTHER PUBLICATIONS

Emil Y. Sidky, et al., "A robust method of x-ray source spectrum estimation from transmission measurements: Demonstrated on computer simulated, scatter-free transmission data", Journal of Applied Physics, vol. 97, Issue 12, 2005, 7 pages (Abstract only).

(Continued)

*Primary Examiner* — Hoon K Song
(74) *Attorney, Agent, or Firm* — Oblon, McClelland, Maier & Neustadt, L.L.P.

(57) ABSTRACT

An apparatus, system and method for calibrating an x-ray apparatus including acquiring sinogram data by scanning a symmetrical phantom using a plurality of detector channels; generating mirror-copied sinogram data by mirror-copying at least one of first sinogram data and second sinogram data of the acquired sinogram data, wherein the first sinogram data and the second sinogram data are generated by dividing the sinogram data at a center detector channel of the plurality of detector channels; outputting a first reconstructed image by reconstructing the mirror-copied sinogram data; and determining a calibration parameter based on the first reconstructed image.

20 Claims, 22 Drawing Sheets

(56) References Cited

OTHER PUBLICATIONS

Xinhui Duan, et al., "CT scanner x-ray spectrum estimation from transmission measurements", Medical Physics, vol. 38, No. 2, Feb. 2011, pp. 993-997.

Jannis Dickmann, et al., "A count rate-dependent method for spectral distortion correction in photon counting CT", SPIE Proceedings, Medical Imaging: Physics of Medical Imaging, vol. 10573, Mar. 9, 2018, 2 pages (Abstract only).

* cited by examiner

1) Generate phantom sinogram with X-ray tube offset angle
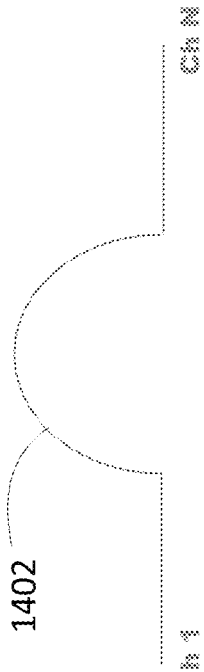
1402
2) Split each projection into left and right halves
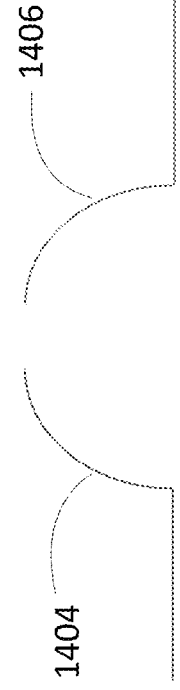
1406
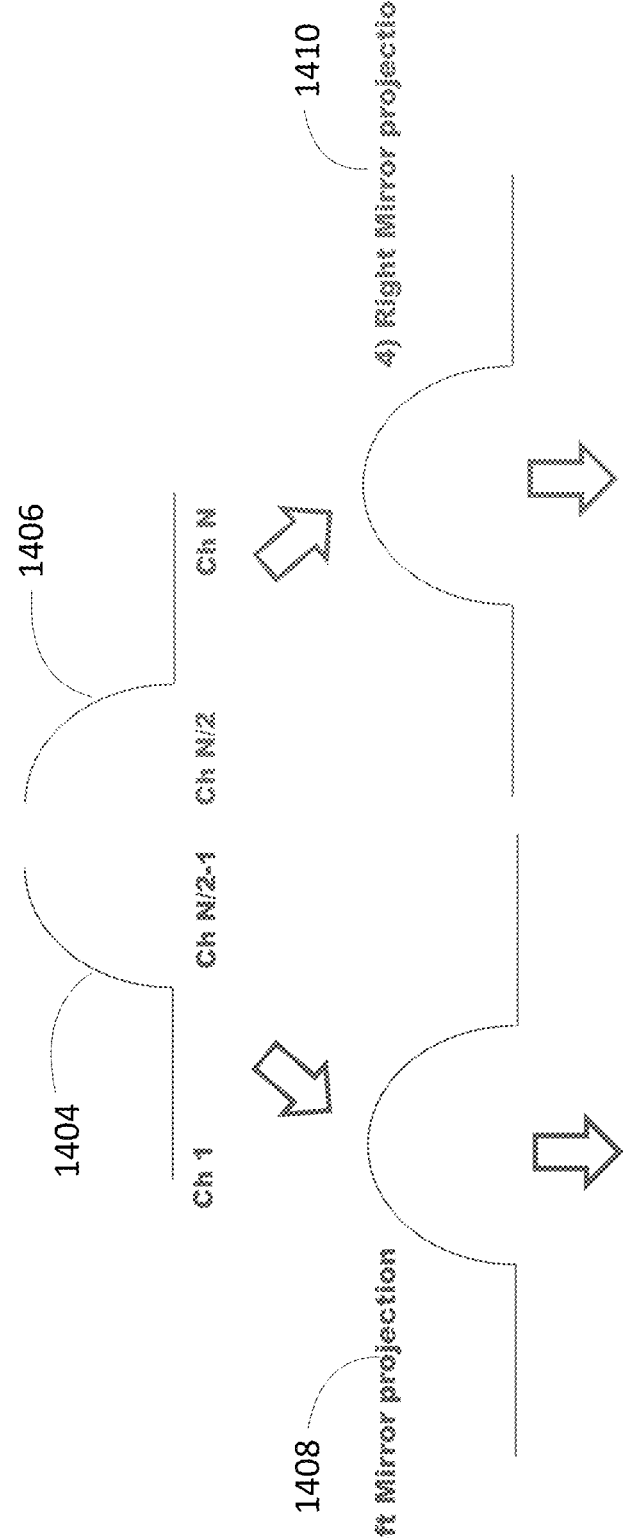
4) Right Mirror projection
1410
6) Reconstruct Right-Mirrored sinogram to image
1414
3) Left Mirror projection
1408
5) Reconstruct Left-Mirrored sinogram to image
1412
Fig. 14

SELF CALIBRATION METHOD AND APPARATUS FOR CORRECTING OFFSET ANGLE IN A PHOTON COUNTING COMPUTED TOMOGRAPHY SYSTEM

FIELD OF THE INVENTION

The disclosure relates to material decomposition in a full size photon counting computed tomography system.

DESCRIPTION OF THE RELATED ART

Computed tomography (CT) systems and methods are typically used for medical imaging and diagnosis. CT systems generally create projection images through a subject's body at a series of projection angles. A radiation source, such as an X-ray tube, irradiates the body of a subject and projection images are generated at different angles. Images of the subject's body can be reconstructed from the projection images.

Conventionally, energy-integrating detectors (EIDs) and/or photon-counting detectors (PCDs) have been used to measure CT projection data. PCDs offer many advantages including their capacity for performing spectral CT, wherein the PCDs resolve the counts of incident X-rays into spectral components referred to as energy bins, such that collectively the energy bins span the energy spectrum of the X-ray beam. Unlike non-spectral CT, spectral CT generates information due to different materials exhibiting different X-ray attenuation as a function of the X-ray energy. These differences enable a decomposition of the spectrally resolved projection data into different material components, for example, the two material components of the material decomposition can be bone and water.

Even though PCDs have fast response times, at high X-ray flux rates indicative of clinical X-ray imaging, multiple X-ray detection events on a single detector may occur within the detector's time response, a phenomenon called pileup. Left uncorrected, pileup effect distorts the PCD energy response and can degrade reconstructed images from PCDs. When these effects are corrected, spectral CT has many advantages over conventional CT. Many clinical applications can benefit from spectral CT technology, including improved material differentiation since spectral CT extracts complete tissue characterization information from an imaged object.

One challenge for more effectively using semiconductor-based PCDs for spectral CT is performing the material decomposition of the projection data in a robust and efficient manner. For example, correction of pileup in the detection process can be imperfect, and these imperfections degrade the material components resulting from the material decomposition.

In a photon counting CT system, the semiconductor-based detector using direct conversion is designed to resolve the energy of the individual incoming photons and generate measurement of multiple energy bin counts for each integration period. However, due to the detection physics in such semiconductor materials (e.g. CdTe/CZT), the detector energy response is largely degraded/distorted by charge sharing, k-escape, and scattering effects in the energy deposition and charge induction process, as well as electronic noise in the associated front-end electronics. Due to finite signal induction time, at high count-rate conditions, pulse pile-up also distorts the energy response, as discussed above.

Due to sensor material non-uniformity and complexity of the integrated detection system, it is difficult to accurately model such detector response for a PCD just based on physics theories or Monte Carlo simulations with a certain modeling of the signal induction process, which modeling determines the accuracy of the forward model of each measurement. Also, due to uncertainties in the incident X-ray tube spectrum modeling, the modelling introduces additional errors in the forward model, and all these factors eventually degrade the material decomposition accuracy from the PCD measurements, therefore the generated spectral images.

Calibration methods have been proposed to solve similar problems in literature. The general idea is to use multiple transmission measurements of various known path lengths to modify the forward model such that it agrees with the calibration measurements. Some ideas are applied on estimation of the X-ray spectrum in conventional CT, see Sidky et al., Journal of Applied Physics 97(12), 124701 (2005) and Duan et al., Medical Physics 38(2), February, 2011, and later adopted on photon-counting detectors to estimate the combined system spectral response, see Dickmann et al., Proc. SPIE 10573, Medical Imaging 2018: Physics of Medical Imaging, 1057311 (Mar. 9, 2018). However, there can be many variations in the detailed design and implementation of the calibration method, especially considering the application feasibility in a full 3rd generation CT geometry.

SUMMARY

Disclosed is a calibration method comprising: acquiring calibration information data by scanning a slab for a plurality of detector channels at an X-ray tube angle. Calibrating a forward calibration model based on the acquired calibration information data at an estimated X-ray tube angle, wherein the estimated X-ray tube angle is an estimate of the X-ray tube angle. Scanning a calibration phantom for the plurality of detector channels to generate sinogram data at the estimated X-ray tube angle based on the forward calibration model. Generating mirrored sinogram data by mirroring a subset of the generated sinogram data on a first side of a line of symmetry, wherein the line of symmetry divides the plurality of detector channels. Outputting a reconstructed image by reconstructing the mirrored sinogram data and the subset of the calibrated sinogram data that are separated by the line of symmetry. Determining a calibration parameter based on the correlation between a portion of the reconstructed image corresponding to the mirrored sinogram data and a portion of the reconstructed image corresponding to the subset of the calibrated sinogram data.

In one aspect, the method further comprising: updating the estimated X-ray tube angle by an offset amount based on the determined calibration parameter. Re-generating the sinogram data based on the updated estimated X-ray tube angle to generate a re-calibrated sinogram data. Generating another mirrored sinogram data by mirroring a subset of the re-calibrated sinogram data on the first side of the line of symmetry. Outputting another reconstructed image by reconstructing the another mirrored sinogram data and the subset of the re-calibrated sinogram data that are separated by the line of symmetry. Determining an updated calibration parameter based on the correlation between a portion of the reconstructed image corresponding to the another mirrored sinogram data and a portion of the reconstructed image corresponding to the subset of the re-calibrated sinogram data.

In one aspect, the method further comprising: determining whether a difference between magnitude of the calibrated sinogram data and the mirrored sinogram data satisfies a threshold value; and storing the determined calibration parameter when the determination indicates that the difference between magnitude of the calibrated sinogram data and the mirrored sinogram data satisfies the threshold value.

In one aspect, the method further comprising: updating the estimated X-ray tube angle by an offset amount when the determination indicates that the difference between magnitude of the calibrated sinogram data and the mirrored sinogram data does not satisfy the threshold value In one aspect, the method further comprising: scanning the calibration phantom at an isocentre by an X-ray scanner system, wherein the calibration phantom is a circular uniform phantom.

In one aspect, wherein the scanning of the calibration phantom is performed by a rotational scan around the circular uniform phantom, wherein the circular uniform phantom is a cylindrical phantom.

In one aspect, the method further comprising: scanning the slab with an X-ray tube located at known locations on an X-ray scanner system, wherein the slab has a known linear attenuation coefficient and a known pathlength. Generating material decomposition data based on the scanning of the slab. Generating air calibration data based on an air scan using the X-ray tube at a rotation speed. Calibrating a forward model for the X-ray scanner system based at least on the material decomposition data and the air scan.

In one aspect, the material decomposition data includes a weighted bin response and a pulse pileup correction term.

In one aspect, the X-ray scanner system is a photon counting CT scanner system.

In one aspect, the X-ray scanner system is a 3rd generation photon counting CT scanner system.

Also disclosed is a system comprising processing circuitry configured to, acquire calibration information data by scanning a slab for a plurality of detector channels at an X-ray tube angle. Calibrate a forward calibration model based on the acquired calibration information data at an estimated X-ray tube angle, wherein the estimated X-ray tube angle is an estimate of the X-ray tube angle. Scan a calibration phantom for the plurality of detector channels to generate sinogram data at the estimated X-ray tube angle based on the forward calibration model. Generate mirrored sinogram data by mirroring a subset of the generated sinogram data on a first side of a line of symmetry, wherein the line of symmetry divides the plurality of detector channels. Output a reconstructed image by reconstructing the mirrored sinogram data and the subset of the calibrated sinogram data that are separated by the line of symmetry. Determine a calibration parameter based on the correlation between a portion of the reconstructed image corresponding to the mirrored sinogram data and a portion of the reconstructed image corresponding to the subset of the calibrated sinogram data.

In one aspect, the processing circuitry is configured to, update the estimated X-ray tube angle by an offset amount based on the determined calibration parameter. Re-generate the sinogram data based on the updated estimated X-ray tube angle to generate a re-calibrated sinogram data. Generate another mirrored sinogram data by mirroring a subset of the re-calibrated sinogram data on the first side of the line of symmetry. Output another reconstructed image by reconstructing the another mirrored sinogram data and the subset of the re-calibrated sinogram data that are separated by the line of symmetry. Determine an updated calibration parameter based on the correlation between a portion of the reconstructed image corresponding to the another mirrored sinogram data and a portion of the reconstructed image corresponding to the subset of the re-calibrated sinogram data.

In one aspect, the processing circuitry is configured to, determine whether a difference between magnitude of the calibrated sinogram data and the mirrored sinogram data satisfies a threshold value; and store the determined calibration parameter when the determination indicates that the difference between magnitude of the calibrated sinogram data and the mirrored sinogram data satisfies the threshold value.

In one aspect, the processing circuitry is configured to, update the estimated X-ray tube angle by an offset amount when the determination indicates that the difference between magnitude of the calibrated sinogram data and the mirrored sinogram data does not satisfy the threshold value.

In one aspect, the processing circuitry is configured to, scan the calibration phantom at an isocentre by an X-ray scanner system, wherein the calibration phantom is a circular uniform phantom.

In one aspect, the scanning of the calibration phantom is performed by a rotational scan around the circular uniform phantom, wherein the circular uniform phantom is a cylindrical phantom.

In one aspect, the processing circuitry is configured to, scan the slab with an X-ray tube located at known locations on an X-ray scanner system, wherein the slab has a known linear attenuation coefficient and a known pathlength, generate material decomposition data based on the scanning of the slab, generate air calibration data based on an air scan using the X-ray tube at a rotation speed, and calibrate a forward model for the X-ray scanner system based at least on the material decomposition data and the air scan.

In one aspect, the material decomposition data includes a weighted bin response and a pulse pileup correction term.

In one aspect, the X-ray scanner system is a photon counting CT scanner system.

In one aspect, the X-ray scanner system is a 3rd generation photon counting CT scanner system.

BRIEF DESCRIPTION OF THE DRAWINGS

The application will be better understood in light of the description which is given in a non-limiting manner, accompanied by the attached drawings in which:

FIG. 14 shows a method of mirroring of a sinogram for a given X-ray tube offset angle.

DETAILED DESCRIPTION OF THE PREFERRED EMBODIMENTS

Reference throughout this specification to "one embodiment" or "an embodiment" means that a particular feature, structure, material, or characteristic described in connection with the embodiment is included in at least one embodiment of the application, but do not denote that they are present in every embodiment.

Thus, the appearances of the phrases "in one embodiment" or "in an embodiment" in various places throughout this specification are not necessarily referring to the same embodiment of the application. Furthermore, the particular features, structures, materials, or characteristics may be combined in any suitable manner in one or more embodiments.

This disclosure relates to a photon counting CT scanner system for material decomposition, said CT scanner system comprising one or more X-ray tubes that emit X-ray radiation, and an array of detector pixels for receiving the X-ray radiation propagating through a field of view of the CT scanning system.

Figure 1:
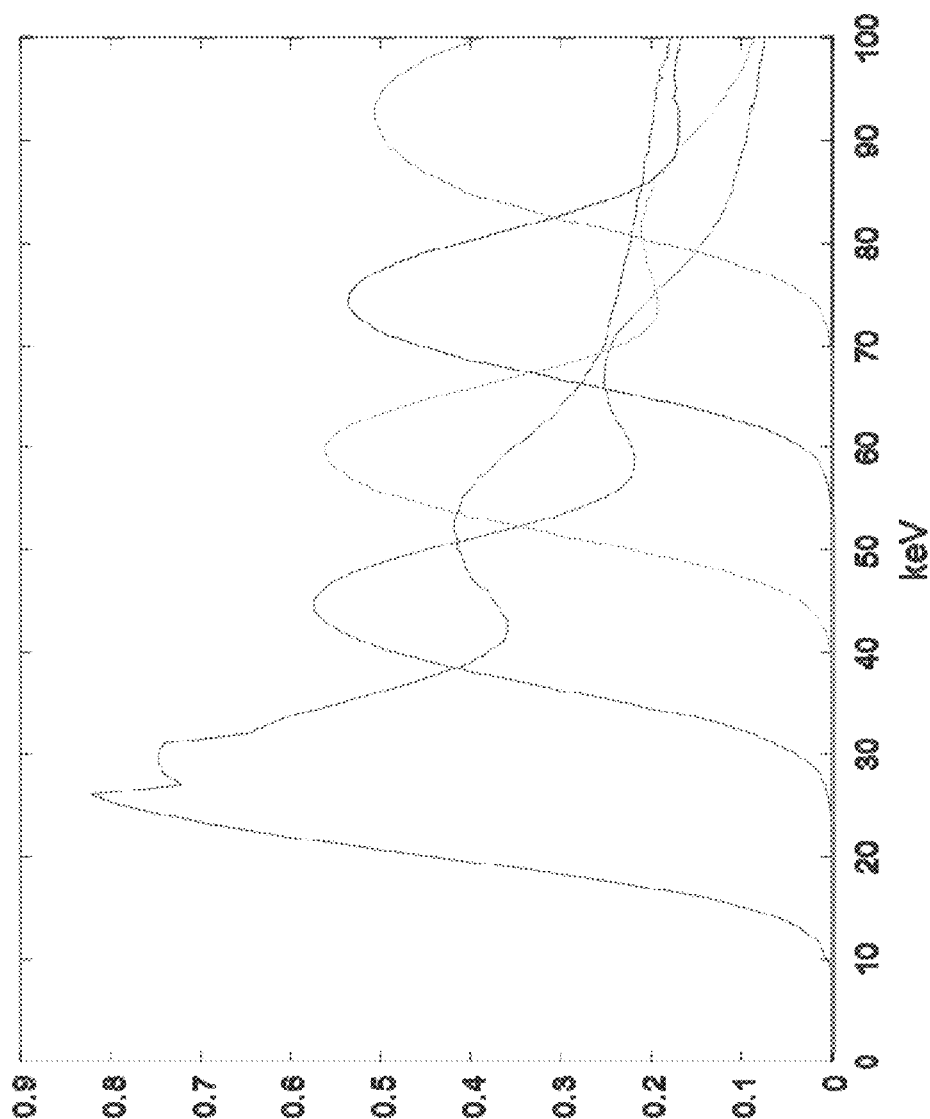
FIG. 1 shows an example of a PCD bin response function $S_b(E)$ for a photon counting detector. Each curve stands for an example function for each energy bin.

In a transmission measurement using a photon counting energy-resolving detector (PCD), the forward model can be formulated as below:

$$N_b(l_1, \ldots,) = N_0 \times \int dE \, w(E) S_b(E) \exp(-\Sigma \mu_m l_m), \quad (1)$$

where $S_b(E)$ denotes the bin response function defined as $S_b(E) = \int_{E_{bL}}^{E_{bH}} R(E, E') dE'$ where $R(E,E)$ is the detector response function, and $E_{bL}$ and $E_{bH}$ are the low and high energy threshold of each counting bin. FIG. 1 shows an example model of a typical $S_b(E)$ function for a PCD, where a long tail above the energy window is induced by charge sharing, k-escape and scattering effect. The low energy tail is mostly due to the finite energy resolution from the associated electronic noise. $N_0$ is the total flux from an air scan, $\mu_m$ and $l_m$ are the $m^{th}$ basis material linear attenuation coefficient and path length. $w(E)$ is the normalized incident X-ray spectrum. In practice, both $w(E)$ and $S_b(E)$ are not exactly known, and they can be combined as one term, $S_{wb}(E) = w(E) S_b(E)$, called thereafter the weighted bin response function. If $S_{wb}(E)$ can be calibrated through measurements, the decomposition problem at low flux condition can be well solved.

For a high flux scan condition (e.g. a few percent of pulse pileup), pulse pileup introduces additional spectral distortion in the measurement. One way to correct for the pileup effect is to introduce additional correction terms (e.g. see Dickmann above, who uses the measured count rate(s) as input). And this type of additional calibration is based on an accurate estimation of the flux independent weighted bin response $S_{wb}(E)$. How to estimate $S_{wb}(E)$ in a full size 3rd generation CT system is a first problem solved in the present application.

At typical CT clinical scan conditions, it is common to encounter a few percent or higher pulse pileup for some measurements. The resulting effect in material decomposition depends on the measured spectrum as well as the flux. Without knowing the actual detector response, one can only do a limited number of transmission measurements to adjust the forward model. For a full CT system in clinical setting, it is crucial to have a feasible calibration procedure. Therefore, how to efficiently parameterize the model and optimize the calibration procedure is the second problem solved in the present application.

Additional practical challenges of conducting such a two-step calibration in a full size CT system include the following: fan-angle dependent weighted spectral response due to beam pre-filtration (e.g. bowtie filters); minimum flux limited due to the X-ray tube operational specifications and fixed system geometry; full detector ring calibration with various detector response across the pixels; limited space for in-system calibration phantom positioning; complication when calibrating on a rotating system with anti-scatter-grids; calibration systematic error and related mechanical design tolerances; non-ideal detectors with uniformity issue on energy resolution, counting, and drifts of the energy threshold settings, etc.

The above non-ideal factors need to be considered for a photon counting CT to reach image qualities competitive to conventional energy integrating detector (EID)-based systems which have much simpler detector response modeling and related calibrations, while maintaining a similar calibration procedure/workflow that does not significantly increase the system down time.

In one non-limiting embodiment, a two-step calibration method for the PCD forward model for material decomposition is applied. The method consists of two parts: 1) estimation of the flux independent weighted bin response function $S_{wb}(E)$ using the expectation maximization (EM) method, and 2) estimation of the pileup correction term $P_b(E, N_b, N_{tot})$ which is a function of energy (E) and the measured bin counts ($N_b$, $N_{tot}$), where $N_b$ is the individual bin count and $N_{tot}$ is the total count of all the energy bins. The calibrated forward model can be expressed as:

$$N_b(l_1, \ldots, M) = N_0 \int^{Emax} dE S_{wb}(E) * P_b(E, N_b, N_{tot}) \exp(-\Sigma \mu_m l_m) \quad (2)$$

Here, instead of using only two materials, the method uses 2-5 different materials such as polypropylene, water, aluminium, titanium/copper, and k-edge materials to calibrate the weighted bin response function $S_{wb}(E)$ at low flux. With more selective materials used in the calibration, the number of total path lengths is reduced to achieve equivalent or better results.

Step 1: With an appropriate tube spectrum modelling to capture the characteristic peaks in the incident spectrum, and a physical model to simulate the photon-counting detector spectral response, an initial guess of $S_{wb}(E)$ can be produced. By using the EM method (e.g., see Sidky), $S_{wb}(E)$ can be reliably estimated for this very ill-conditioned problem based on a few transmission measurements.

Here, $P_b(E, N_b, N_{tot})$ is assumed to be constant in Step 1. The calibrated forward model can be simplified to a system of linear equations $$N_b(l_1, \ldots, l_M) = N_0 \int^{E_{max}} dE S_{wb}(E) \exp(-\Sigma \mu_m l_m) \quad (3)$$

Usually, the number of data measurements (M) is much smaller than the number of unknowns ($E_{max}$). With the assumption of Poisson distribution of the data acquisition, an iterative EM algorithm can be derived to find the optimal estimation of the unknown energy bin response function $S_{wb}(E)$, as described below.

When estimating the bin response function using low flux data acquisition, the pileup effect correction $P_b$ is assumed to be a known term (e.g. constant). So, the model is simplified to $$N_b = N_0 \int dE S_{wb}(E) [\exp[-\Sigma \mu_m(E) l_m]] \quad (4)$$

Let $A^j(E) = \exp[-\Sigma \mu_m(E) l_m^j]$ represent the attenuated pathlength for j-th measurement. Thus, for each measurement j, we have $$N_b^j = N_0 \int dE S_{wb}(E) A^j(E) = N_0 \Sigma_E S_{wb}(E) A^j(E) \quad (5)$$

With M measurements, the data acquisition can be written in the matrix form below $$N_0 \begin{pmatrix} A^1(1) & \cdots & A^1(E_{max}) \\ \vdots & \ddots & \vdots \\ A^M(1) & \cdots & A^M(E_{max}) \end{pmatrix}_{M \times E_{max}} \cdot \begin{pmatrix} S_{wb}(1) \\ \vdots \\ S_{wb}(E_{max}) \end{pmatrix}_{E_{max} \times 1} = \begin{pmatrix} N_b^1 \\ \vdots \\ N_b^M \end{pmatrix}_{M \times 1}$$

or $A \cdot S_{wb} = N_b$

By applying the EM iterative algorithm, the $S_{wb}$ can be estimated by $$S_{wb}^{(k+1)} = S_{wb}^{(k)} \odot ((A^T \cdot (N_b \oslash (A \cdot S_{wb}^{(k)}))) \oslash (A^T \cdot 1)) \quad (6)$$

where
k: iteration number
·: matrix multiplication
⊙: element-wise multiplication
⊘: element-wise division
1: vector of ones with size of M×1
the updating formula for $S_{wb}(E)$ is given by $$S_{wb}^{(k+1)}(E) = S_{wb}^{(k)}(E) \frac{\Sigma_{j'} A^{j'}(E) \frac{N_b^{j'}}{\Sigma_{E'} A^{j'}(E') s_{wb}^{(k)}(E')}}{\Sigma_{j'} A^{j'}(E)} \quad (7)$$

Step 2: Once $S_{wb}(E)$ is estimated from the calibration at each tube voltage (kVp) setting for each detector pixel, it is saved as a software calibration table on the system. It will be used as an input to further estimate the pileup correction terms $P_b(E, N_b, N_{tot})$ at higher flux scans. Both tables are then used for the material decomposition in object/patient scans to estimate the basis material path lengths.

The calibration tables are updated from time to time based on the system/detector performance variations. This can also be designed as an iterative procedure. If the image quality is not good enough on a quality check phantom, this calibration process is repeated with the updated calibration tables from the last iteration as the initial guess.

Figure 2:
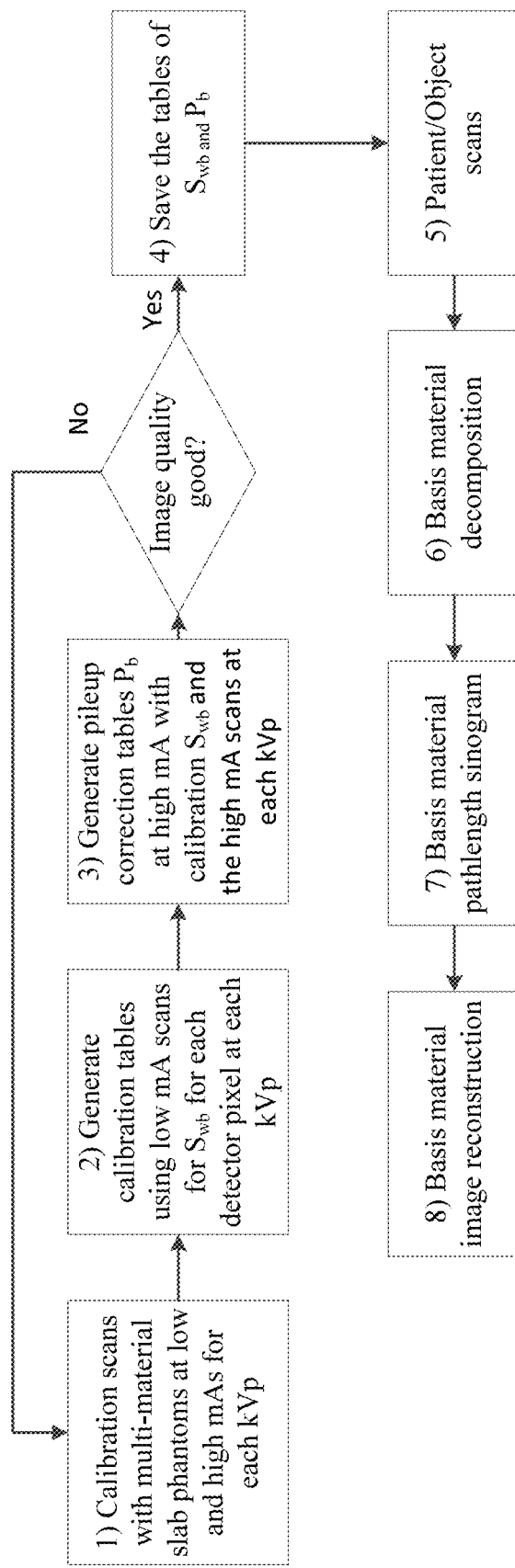
FIG. 2 shows a material decomposition calibration and processing workflow.

The high level workflow of the above process is demonstrated in FIG. 2. Steps 1) to 4) represent the calibration workflow, and steps 5) to 8) demonstrate how the calibration tables are used in the operational scans of patients/objects to produce spectral images.

First, a series of low flux scans on various material slabs are collected at each tube kVp setting, which is the peak potential applied on the X-ray tube. Typical CT systems support a few kVp settings from 70 to 140 kVp which generate different energy spectrums from the X-ray tube for different scan protocol. For a CT scan, both mA and kVp need to be pre-selected before the tube is turned on. Then, the low flux weighted bin response function $S_{wb}$ is estimated and with the estimated $S_{wb}$, the high flux slab scans are used to estimate the additional parameters in the pileup correction term $P_b$. With the estimation calibration tables of $S_{wb}$ and $P_b$ for each detector pixel, the quality of the calibration is checked on a quality phantom, e.g. a uniform water phantom, or phantom with multiple inserts with uniform known materials. The image quality is assessed with predefined standards, and if it is passed, the current calibration tables are saved and then used for the following patient/object scans data processing. Otherwise, the procedure goes through the first three steps again using the last iteration of $S_{wb}$ and $P_b$ as the initial guess. Here, commonly examined standards are: image CT number accuracy, uniformity, spatial resolution, noise and artifacts. To check the quality of this calibration, these metrics should all be checked, especially the accuracy and artifacts like ring or bands in the image, which indicate the calibration is not good enough.

Figure 3:
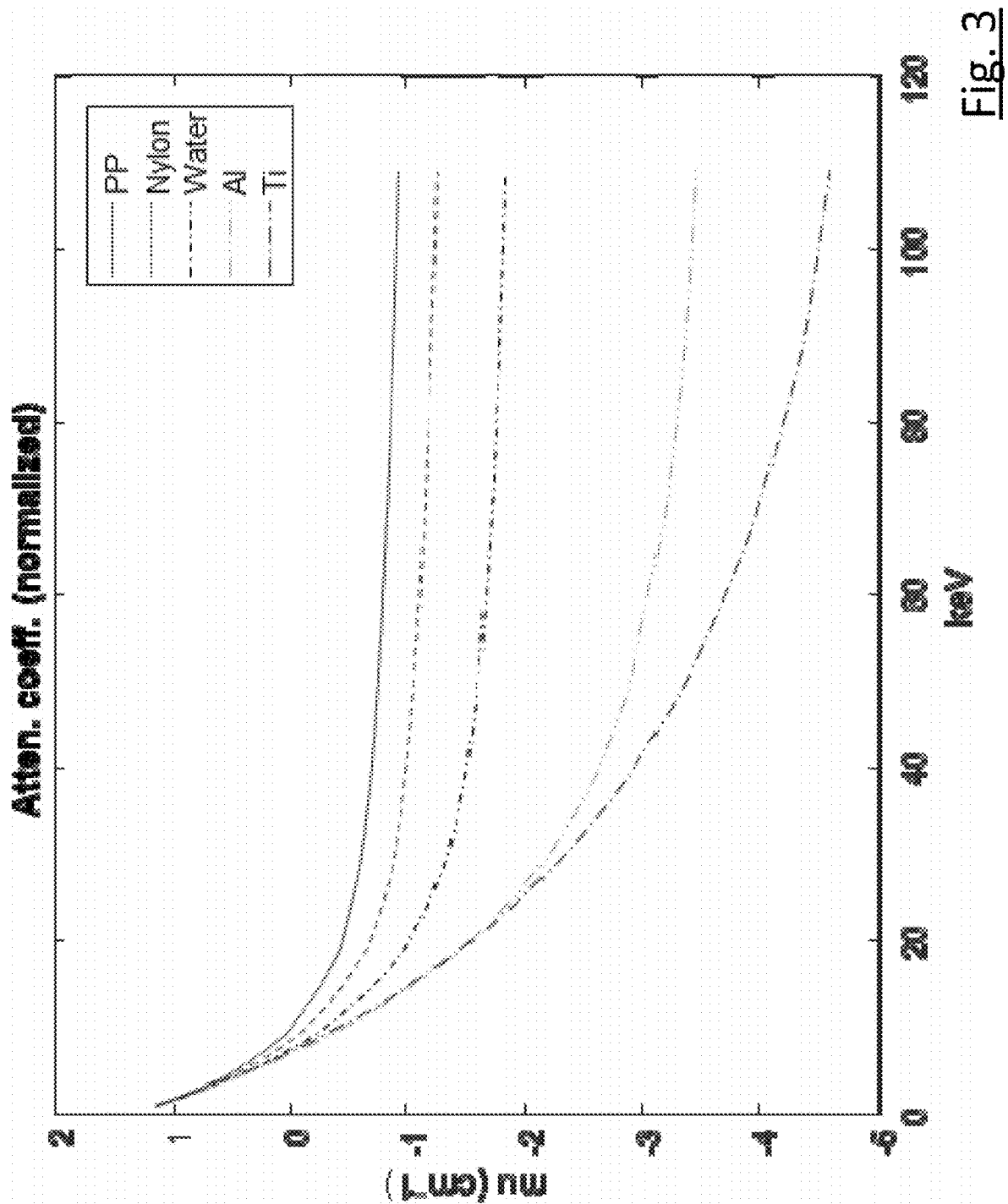
FIG. 3 shows normalized linear attenuation coefficients for different materials.

To choose the optimal materials and path lengths for this calibration, one can use the normalized linear attenuation coefficient vs. energy curves (FIG. 3) to choose the ones that are different from each other, e.g. polypropylene, water, aluminum, titanium can be a good group of combinations for such calibrations which covers a large range of common materials present in human body.

In order to satisfy the low flux condition through the calibration measurement to minimize the pileup effect in the flow diagram, step 1, one can select to use $n\tau < x$, where $x \sim 0.005 - 0.01$ and n is the pixel count rate with the lowest tube flux setting, and $\tau$ is the effective dead time of the PCD Application Specific Integrated Circuit (ASIC). By satisfying this condition, one can calculate the shortest path length of each selected calibration material, and the rest of path lengths can either be selected by equal spacing in path length or in resulting measurement count rate.

Figure 4:
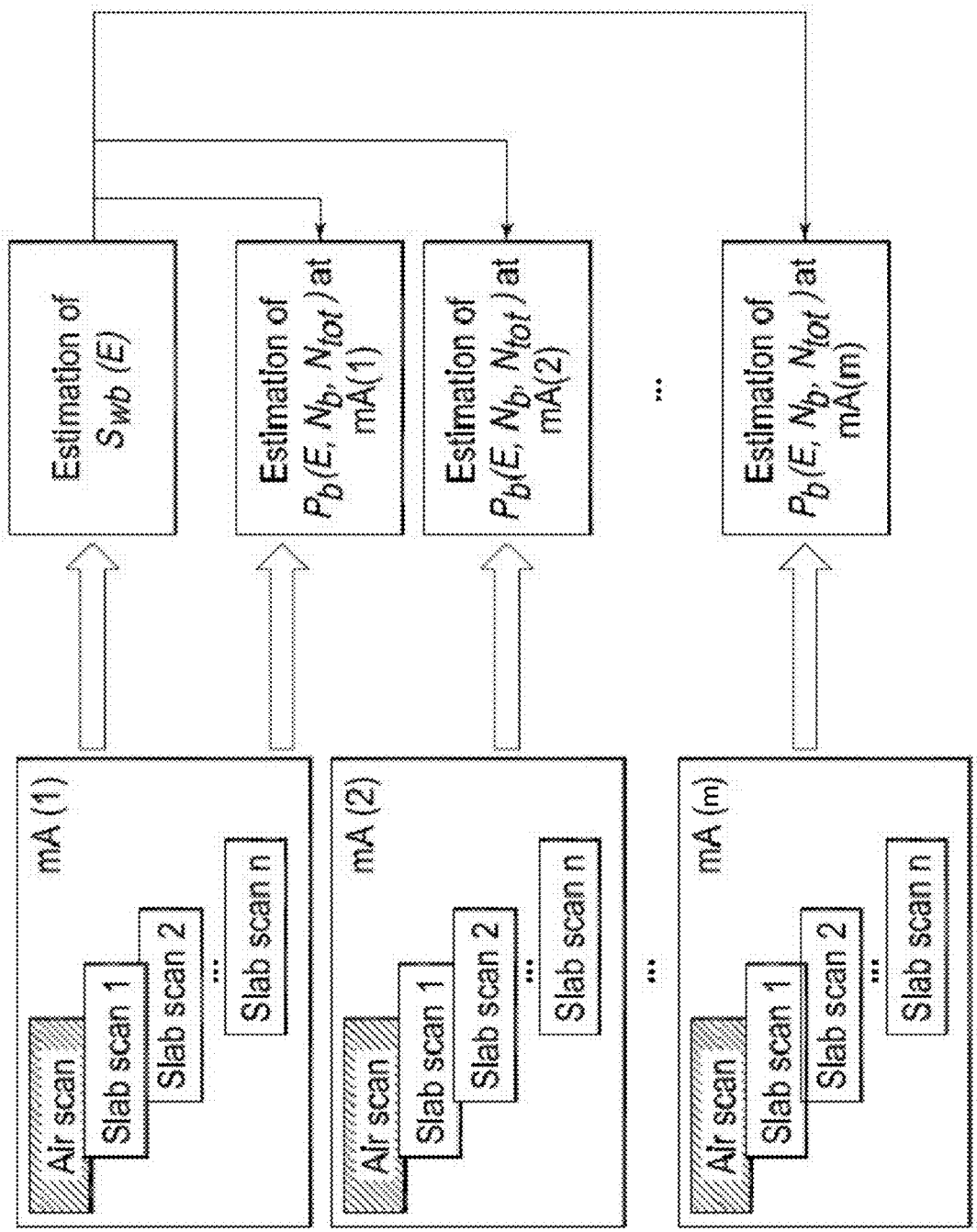
FIG. 4 shows a schematic of a calibration structure design, where the pileup correction tables $P_b$ are generated and used for each mA individually.
Figure 5:
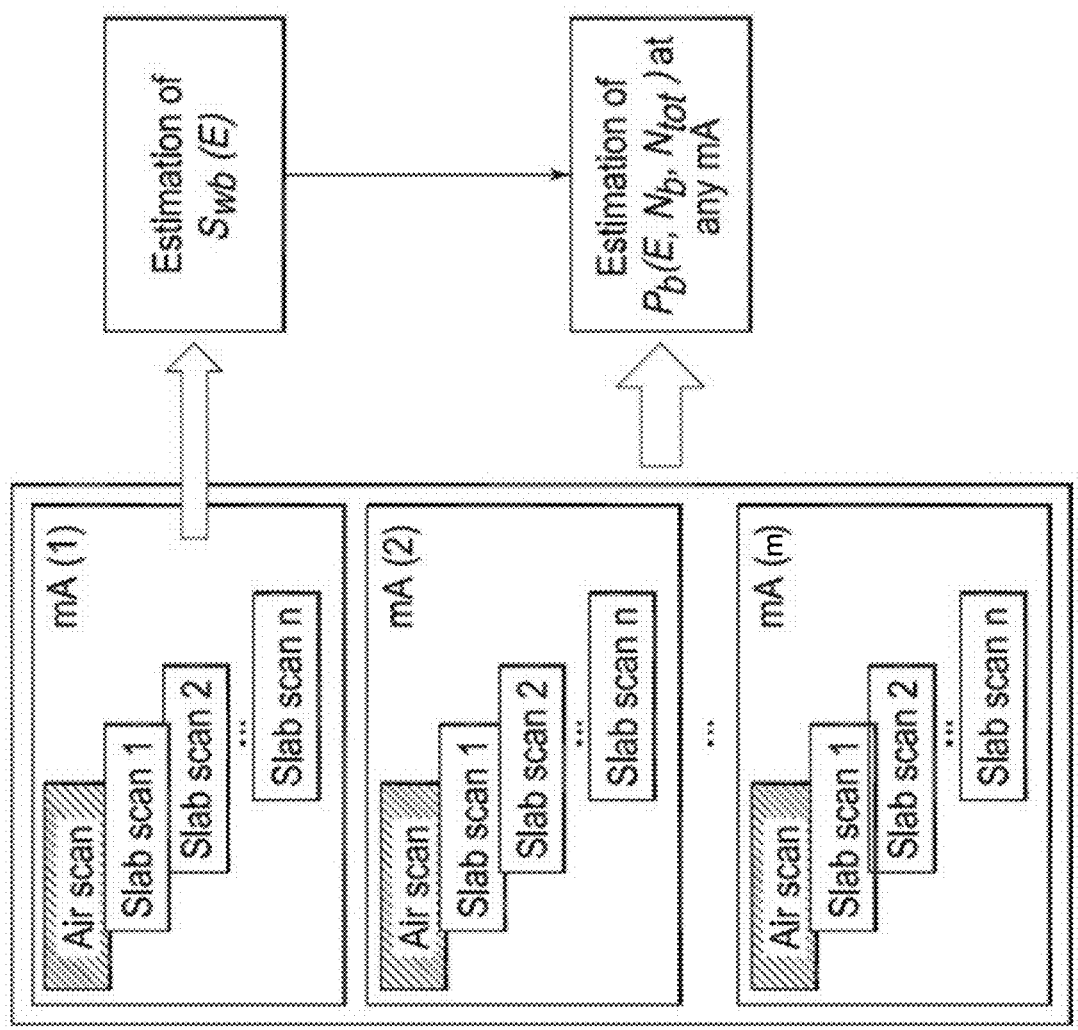
FIG. 5 shows a schematic of another calibration structure design, where a universal pileup correction table $P_b$ is generated for the entire current (mA) range.

For calibration of the pileup correction term $P_b$ in step 3, the same slab material and path lengths are used for scans at high mA settings. The calibration data can be grouped for each mA and generate different correction tables for each mA setting (FIG. 4), or include measurements at all flux ranges (e.g., from low to high mA, from high to low mA, or with most frequently used values first) to generate a universal correction table for a continuous mA setting (FIG. 5).

The calibration measurements should be taken with sufficient statistics to minimize the influence of the statistical fluctuation. One non-limiting example is to use >1000 times more statistics as the typical integration period for the calibration data sets to minimize the transferred statistical error in the calibration. Each energy bin b of the calibration measurements will be used to update the corresponding $S_{wb}(E)$ and $P_b(E, N_b, N_{tot})$.

Since one can only do limited number of measurements with a few energy bins, the estimation is very ill-conditioned. In this case, a good initial guess is crucial for an accurate estimation as it provides additional constraints for the EM method. One of the design variations to accommodate non-ideal detectors is to allow a more flexible energy window for each bin in the initial guess of $S_b$, especially with small variations in the actual energy threshold setting of the ASIC. By setting the low threshold x keV lower, and high threshold y keV higher, the initial $S_b$ becomes:

$$S_b(E) = \int_{EbL-x}^{EbH+y} R(E,E')dE' \tag{8}$$

where x, y can be chosen between 5 to 10 keV to allow certain variations in the ASIC performance, while still providing additional constraints for the EM problem.

The design described in the present application employs more than two materials in the calibration, which provides more sensitivity to constraint the weighted bin response function estimation problem of the photon counting detectors.

In addition, the method utilizes a different parameterization for the high flux pileup correction terms $P_b$ which is now a function of E, $N_b$ and $N_{tot}$. The total count term $N_{tot}$ is introduced for a better approximation of the true pileup phenomena, and can significantly improve the model capability at higher flux condition with fewer parameters.

In addition, it is further possible to calculate an initial guess of the weighted bin response function by enlarging the energy threshold window, to accommodate non-ideal detector/ASIC performance.

A two-step calibration method for a PCD forward model for material decomposition is proposed. It consists of two parts: 1) estimation of the flux independent weighted bin response function $S_{wb}(E)$ using the state of the art EM (expectation maximization) method; and 2) estimation of the pileup correction term (E, $N_b$, $N_{tot}$), which is a function of energy (E) and the measured bin counts $P_b$ ($N_b$, $N_{tot}$), where $N_b$ is the individual bin count and $N_{tot}$ is the total count of all the energy bins. The calibrated forward model can be expressed as shown in Equation (2).

Furthermore, to calibrate the forward PCD measurement model in Equation (2), in one embodiment, at least one slab of at least one predetermined material and known thickness is placed level in the CT scanner's field of view. By using a slab of predetermined material, the linear attenuation coefficient of the slab may be known. Further, by knowing the thickness of the slab, X-ray radiation path lengths through the slab may be known. The slab measurements can be performed by stationary scans where the X-ray tube is parked at a fixed location on the CT scanner and operating at various flux levels.

In one embodiment, the slab scans can also be taken at multiple fixed X-ray tube locations to increase the path length samples and coverage using the same slabs.

To apply for the patient/object scans when gantry is rotating, additional air scans can be taken at each rotation speed to correct for the additional shadow effect for each pixel when the anti-scatter-grid (ASG) is deflected under rotation. The air scans could produce air calibration tables, which may include data on the number of photons that arrive, per integration period, for each pixel.

For a full ring calibration in a 3rd generation geometry, due to the bowtie filtering and typical scanning object shape, the path length of the calibration materials for peripheral detectors may be designed differently from central detectors. Thinner path length ranges could be used towards the edge of the fan beam, and a relationship of the path lengths range for each material can be derived based on the material and shape of the bowtie filter. Additionally, a multi-material slab phantom may be designed to implement the calibration measurements.

Figure 6:
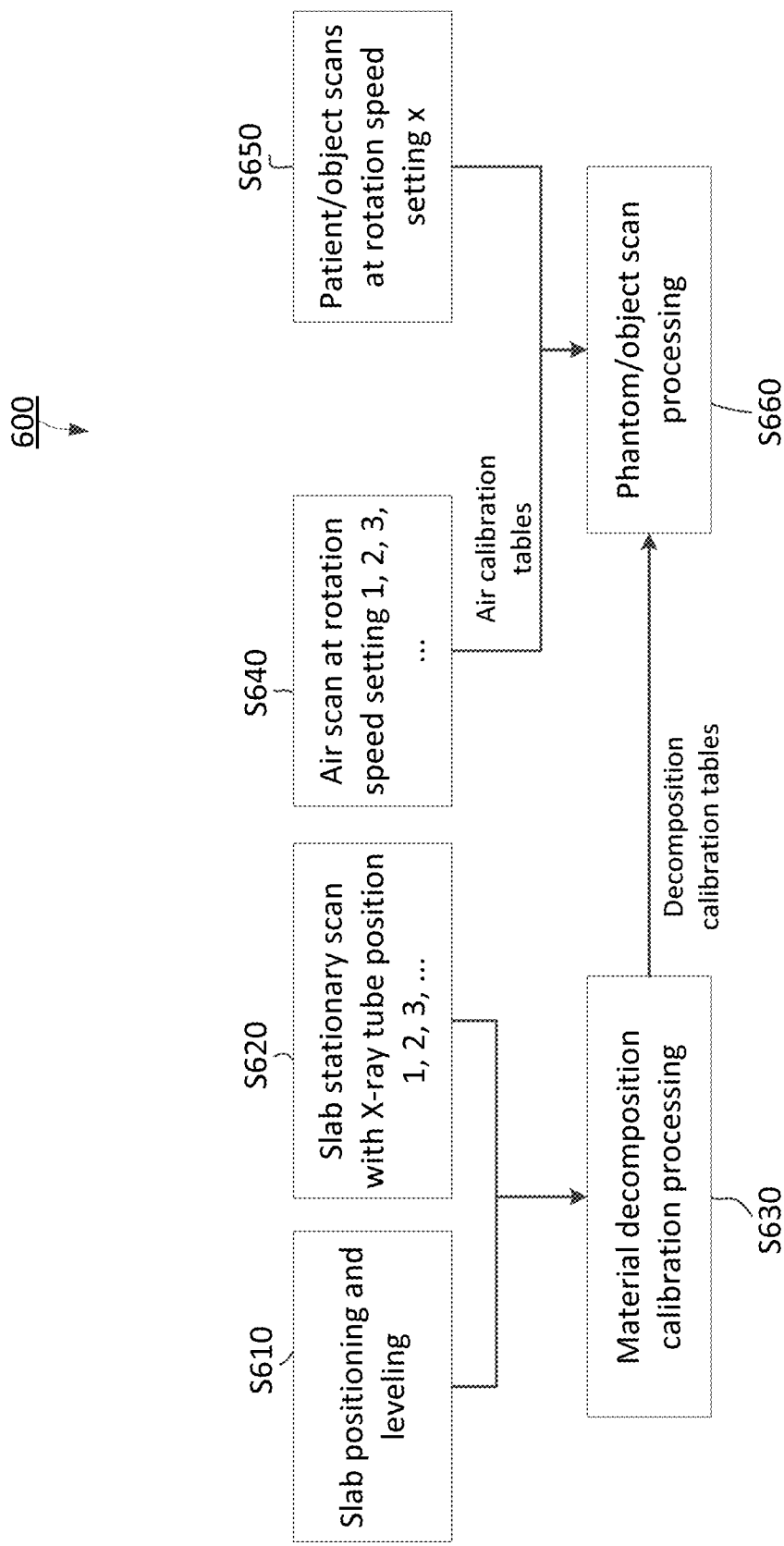
FIG. 6 shows a calibration scan procedure.

FIG. 6 shows one embodiment of a calibration method 600. In step S610, a slab of known material is first positioned and levelled on a CT scanner's patient couch such that path lengths are known and controlled. Then, in S620, one or more stationary X-ray tubes positioned on the CT gantry (e.g. three different X-ray tubes at three different positions) scan the slab. From the scans, in next step S630, material decomposition calibration processing is performed to produce decomposition calibration tables, as mentioned above. Furthermore, in S640, air scans are performed at a range of rotation speeds to produce air calibration tables. In S650, patient/object scans (at a known rotation speed) can be gathered. The decomposition calibration tables, air calibration tables, and patient/object scans can then be used in S660 for phantom/object scan processing and utilize a calibrated forward model.

The range of the slab calibration path length (L) may be designed to cover the maximum attenuation length in clinical scans (e.g. $L_{water}$=0.1-40 cm, $L_{bone}$=0.1-10 cm). This can be estimated through a group of representative clinical scans for different scan protocols. This range can be fan angle dependent, as the edge of the field of view (FOV) usually goes through much less attenuation compared to the center due to the typical patient shape and size. The selection of the calibration path length range can depend on different imaging task which focus on different anatomy. The calibration path length range can also be universal across the fan angle to better cover the abnormal case where the patient is either oversized or needs to be largely shifted from the iso-centre. In other words, various calibration path length ranges may be used at different fan angles to improve the calibration accuracy and efficiency. The slab scans used for the forward model calibration can be selected based on the imaging task to generate the best image quality.

Figure 7:
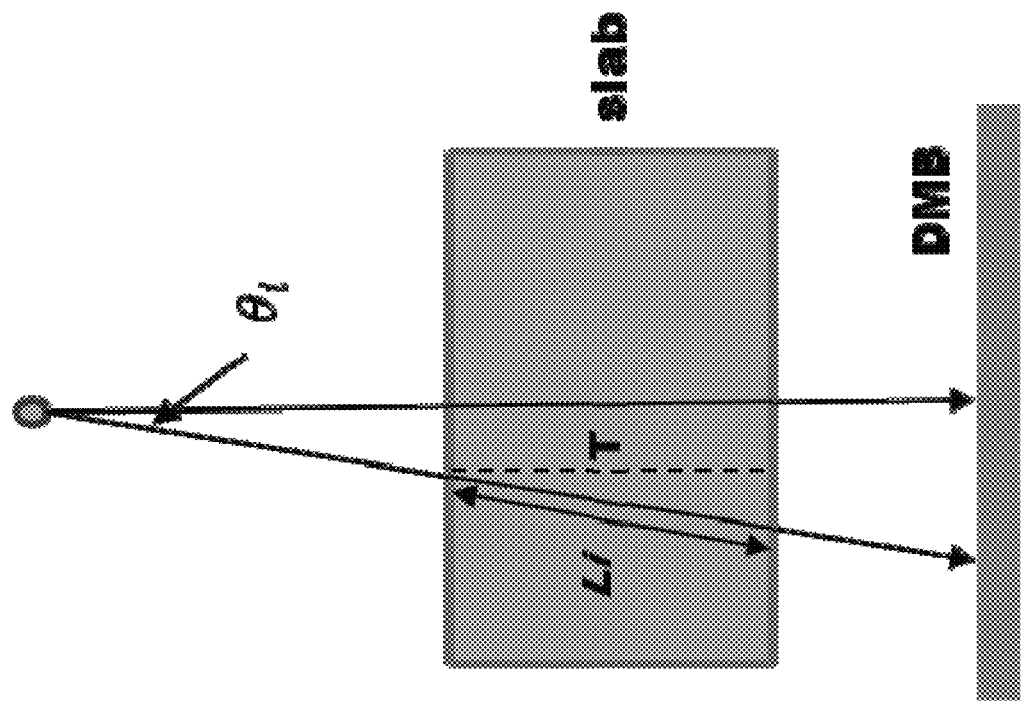
FIG. 7 illustrates calibration slab path lengths at different detector pixels.

With a typical fan beam coverage in a 3rd generation CT, flat slabs are used for this calibration with slightly different actual path lengths across the detector array, as shown in FIG. 7. The actual path lengths $L_i$ for each detector pixel of these calibration scans can be calculated by:

$$L_i = T/\cos\theta_i \tag{9}$$

where T is the thickness of the calibration slab, and $\theta_i$ is the projected fan angle of detector pixel i on a detector module blade (DMB), wherein the DMB consists of rows and channels.

In order to minimize the path length error, calibration with different slabs and thicknesses may be done using a static scan configuration without rotation. The slabs should be large enough to cover the entire detector array and kept well levelled during the entire data acquisition. If for thick slabs, the CT gantry bore size does not allow for a single slab position to cover the entire detector surface, the slab position can be adjusted and multiple scans can be used to cover the entire detector surface. In another embodiment, the calibration with different slabs and thickness may be done using a scan configuration with rotation.

The additional system variations (e.g. tube flux, ASG shadow, etc.) with different rotation speed may be captured by air scans and a reference detector, and corrected accordingly in the air flux term $N_0$ of the forward model. For example, air scans at each rotation speed may be performed prior to the patient/object scan to calibrate the ASG deflection, as well as other beam path variations during rotation that induce the incident flux variation across the detector at different views.

Figure 8:
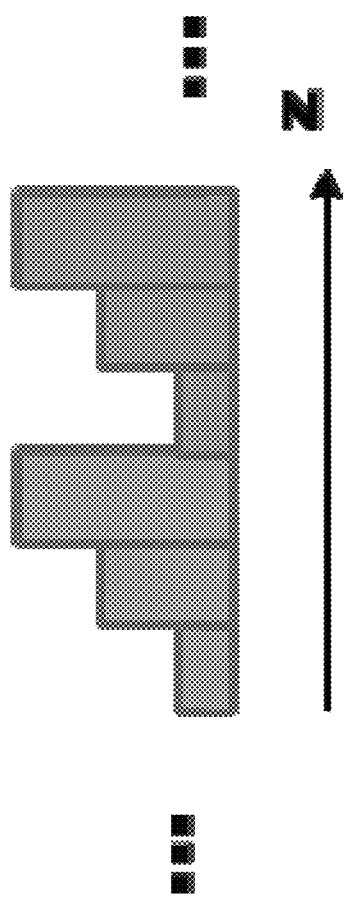
FIG. 8 shows an example of a calibration slab design where calibration slabs are lined up in a Z-direction along at least a portion of a patient couch or other movable mechanism within the detector field.

Referring to FIG. 8, the various calibration slabs can be combined together in a direction along at least a portion of the length of the patient couch to become a long "wedge-like" phantom, so that by moving the position of the couch (or whatever transport mechanism is conveying the slabs), each calibration path length can be detected without re-aligning the phantom, thereby accelerating the calibration process.

Figure 9:
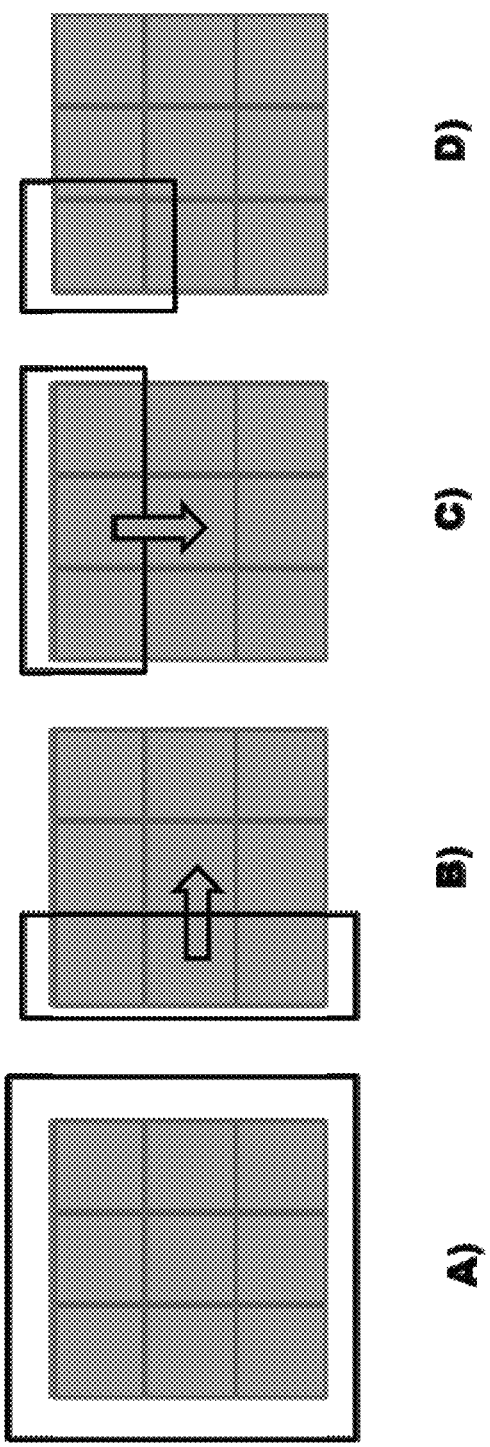
FIG. 9 shows various summing schemes that may be used for decomposition calibration and processing.

To capture the spectrum variation across the fan beam after bowtie filter and detector response variation across different detector pixels, this calibration process may be done pixel by pixel with each bowtie/filter configuration. For a combined-pixel mode ($N_T \times N_C$), this calibration can be done based on the measurement of the sum (or average) of combined pixels for each filter configuration. For example, FIG. 9 shows various summing schemes for decomposition calibration and processing, where the following object scan material decomposition can choose to use one of the summing patterns with the corresponding calibrated tables. The illustrated summing schemes in FIG. 9 are A) summing over the macro-pixel pitch, e.g. 3×3 combined mode, B) summing over the row direction, e.g. 1×3 combined mode, C) summing over the channel direction, e.g. 3×1 combined mode, and D) calibration based on individual micro pixel, e.g. 1×1.

Figure 10:
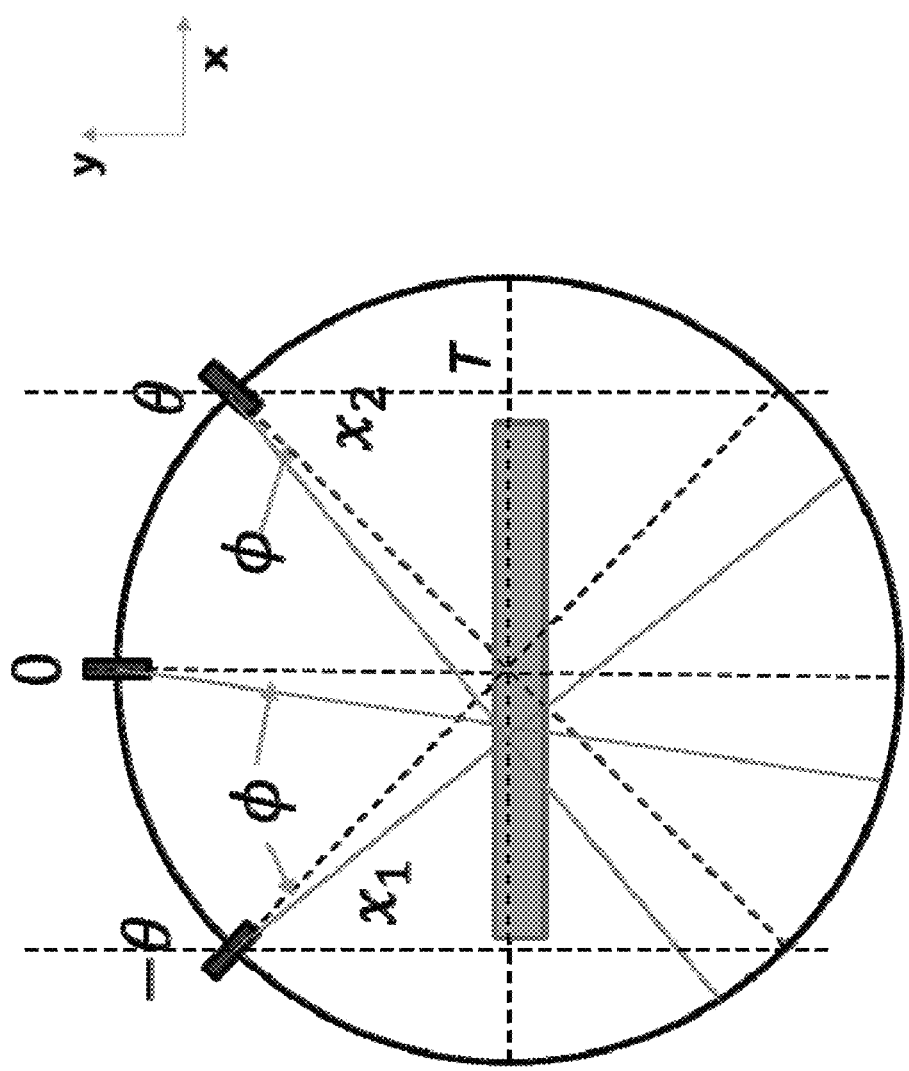
FIG. 10 is a schematic that shows how different X-ray tube locations can generate different path lengths for a slab scan during calibration.

To increase the calibration path length combinations for each slab configuration, the X-ray tube can be positioned at various locations while the slabs are fixed and levelled in the X-Y plane, as illustrated in FIG. 10, which is a schematic showing how multiple tube locations can generate different path lengths for the slab scan in this calibration. As an example, for a given slab thickness T, at detector pixel i, which is located at fan angle $\emptyset_i$, when the tube is placed at different positions (−θ, 0, θ), the measured path lengths are given by:

$$L_i(-\theta) = \frac{T}{\cos(x_1)};$$

$$L_i(0) = \frac{T}{\cos(\phi)};$$

$$L_i(\theta) = \frac{T}{\cos(x_2)};$$

where $x_1 = \theta - \phi$, $x_2 = \theta + \phi$. In one embodiment, the typical range of $\phi$ could be between 0 to 25 degree, and θ can be selected between 20 to 60 degrees depending on the slab thickness intervals. By using this park and shoot scheme, it can triple the path length samples for most of the detector channels, hence, greatly reduced the number of calibration slabs needed to cover the same or larger path length range. The tube can also park at more than three positions to further increase the calibration samples, following the same calculation method described above. For a wide cone coverage system, the calibration path length needs to be calculated based on the projected angle at both the channel and the row direction.

In one embodiment, the slabs are flat and kept levelled during the calibration; this is because it reduces/controls the uncertainty of the path length. In another embodiment, the slabs do not necessarily have to be flat nor level, so long as the path lengths are known and controlled. Further, in one embodiment, each of the slabs are made up of a single material. In another embodiment, the slabs do not always have to consist of a single material. For example, a slab could comprise multiple materials. Examples of materials for a slab can include polypropylene, water, aluminium, titanium/copper, tissue surrogates, other polymers, stainless steel or other metals, k-edge materials, and various tissue mimicking materials.

FIG. 7 that was previously explained above illustrates a 3rd generation CT that includes flat slabs used for stationary scans to calibrate a PCD forward model. This calibration of the PCD forward model may include measurement errors that occur during measurement of various parameters while performing the stationary scans. These measurement errors during stationary scan configuration impact the calibration accuracy. These measurement errors result in measurement values that are different from the actual measurement values that cause errors in calibration, thus causing image quality artifacts in outputted images. One of the measurement parameters while performing the stationary scan is slab path length. Any error during the measurement of the slab path length, also referred to as slab path length error, directly impacts the calibration accuracy. To measure a slab path length, a slab thickness is measured as well as a ground truth path length is measured. Since the measurement of slab thickness can be controlled and measured very well, slab path length can be measured accurately. However, measuring the ground truth path length may cause an error. The error in measurement of ground truth length also referred to as ground truth path length error is difficult to correct because, ground truth path length error may occur due to an error in measurement of a relative position between the slab and the transmission projection during the stationary scans, also referred to as a measured tube parking position. Thus, the slab path length error is introduced because of an error in the tube parking position measurement which introduces a systematic error in the incident angle for measurement at each detector pixel, thus impacting the calibration accuracy during stationary scan configuration.

Figure 11:
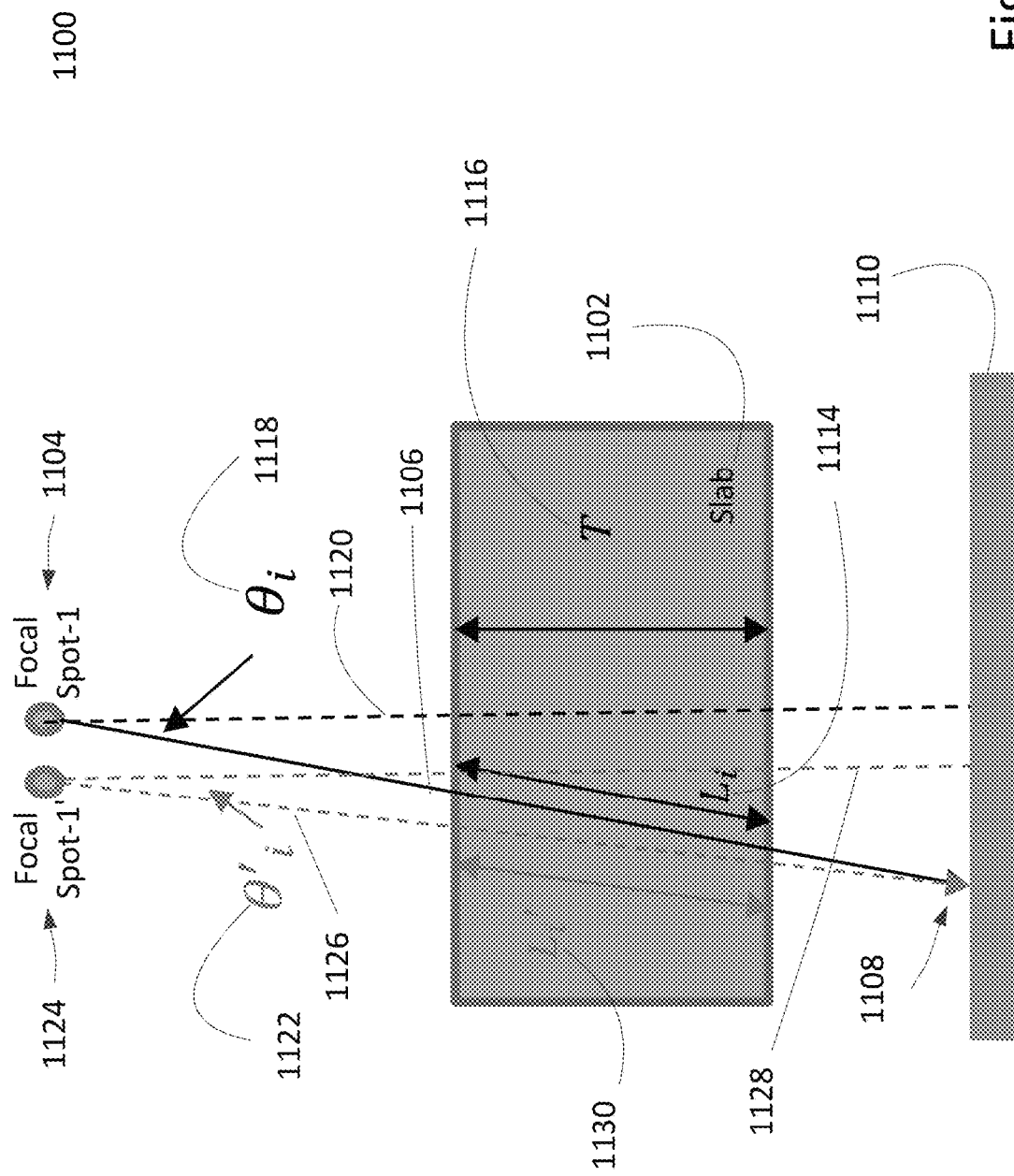
FIG. 11 illustrates calibration slab path lengths at different detector pixels based on an angular offset in measurement.

FIG. 11 illustrates an error in a measured tube parking position in a stationary scan configuration 1100 for a flat slab 1102. FIG. 11 shows a few degrees of angular offset in measurement causes an error in the measurement of the ground truth path length, thus, causing image quality artifacts in the operational scan images. In an embodiment, calibration accuracy during stationary scan configuration is performed with an actual path length and an offset path length across the detector array, as explained in detail below.

A radiation from a focal spot-1 1104 is incident onto the flat slab 1102. Radiation path 1106 indicates the radiation from focal spot-1 1104 passing through the flat slab 1102 and being detected by a pixel "i" at a location 1108 of a radiation detector 1110. Radiation detector 1110 consists of rows and channels of detector pixels. Upon detecting the radiation 1106 by the radiation detector 1110, a processing module coupled to the radiation detector 1110 calculates an actual path length $L_i$ 1114 for detector pixel i. $L_i$ can be calculated by:

$$L_i = T/\cos \theta_i \qquad (10)$$

Where T 1116 is the thickness of the calibration flat slab 1102, and $\theta_i$ 1118 is the projected fan angle of detector pixel i between the incident radiation 1106 and a normal 1120 to the radiation detector 1110.

Figure 12:
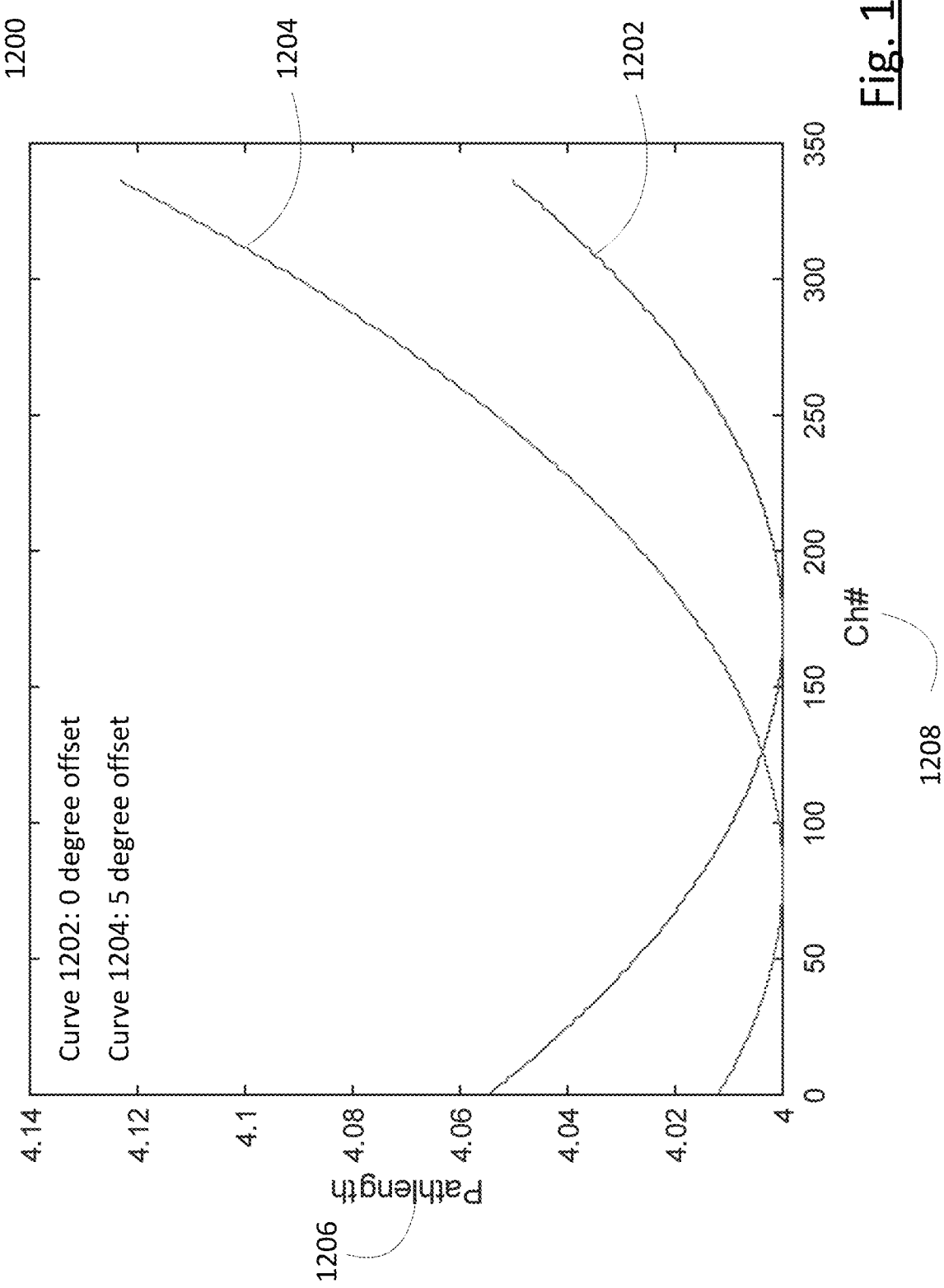
FIG. 12 is a graph illustrating effective path lengths to various detector channels for two different angular offsets.

Further, in a situation where there is a few degrees of angular offset $\theta_i'$ 1122 in the measured tube parking position. In this situation, the focal spot-1 1104 is shifted to focal spot-1' 1124 because of an error in measurement of tube parking position, where, $\theta_i'$ 1122 is the projected fan angle of detector pixel i on the radiation detector 1110 between the incident radiation 1126 and a normal 1128 to the radiation detector 1110. Further, this offset $\theta_i'$ 1122 of few degrees causes a measurement error in the path length $L_i'$ 1130 and further causes an error in the ground truth path length which is then transferred to the operation scan images through the mis-calibrated forward model, causing image quality artifacts in the outputted operational scan images. With reference to FIG. 12, a graph 1200 is illustrated showing two curves 1202 and 1204, each representing effective path lengths to various detector channels for two different angular offsets from a tube parking position. The first curve 1202 assumes a nominal tube position at 0 degree offset and has a path length $L_i$. The second curve 1204 represents a situation when the tube is slightly shifted by 5 degrees. In doing so, the path length is now shifted to $L_i'$, by a factor $f_i$ which is a function of the detector channel fan angle $\phi_i$ and $\tau$:

$$f_i(\phi_i,\tau)=\cos(\phi_i+\tau)/\cos(\phi_i)$$

$$L_i'=L_i*f_i \qquad (10)$$

FIG. 12 shows an example of the calculated path lengths 1202 and 1204 of a slab with thickness T of 4 cm across the detector channels 1208 when the X-ray tube angle is 0 degrees and 5 degrees, respectively. As illustrated, there is a clear difference in calculated path lengths between the two curves 1202 and 1204.

Specifically, when the x-ray tube angle is zero, the curve 1202 indicates an ideal situation with no error in measurement where the path length $L_i$ is determined to be slightly below 4.06 cm and the detector channel with the minimum path length is centered at approximately detector channel 160 out of the total 320 channels. In general, as the detector channel numbers increase from 0, the path length values of curve 1202 initially decrease until the minimum path length occurs (at approximately detector channel 160) and then begins increasing again until a detector channel corresponding to a maximum angle is reached.

Further, when the X-ray tube angle 5 degrees, curve 1204 initially starts at a path length of about 4.01 at detector channel number 0. The path length values of curve 1204 initially decrease as the channel numbers increase and, after reaching a channel number of approximately 75, the path length values begin to increase again. This curve offset indicates that the gantry/tube is offset more towards the lowered numbered channels causing an error in measurement.

Further, in an configuration [not shown in drawings] in which the gantry/tube is offset towards an opposite direction, i.e., towards a higher channel number, then the left side of a corresponding path length curve would begin at a high path length value, and the path length value initially decreases until a minimum path length occurs, and then increase again causing the curve to be disproportionately higher on left side in comparison to the right side of the graph 1200. Such an imbalance would indicate that the gantry/tube is offset more towards the higher numbered channels also causing an error in measurement.

Figure 13:
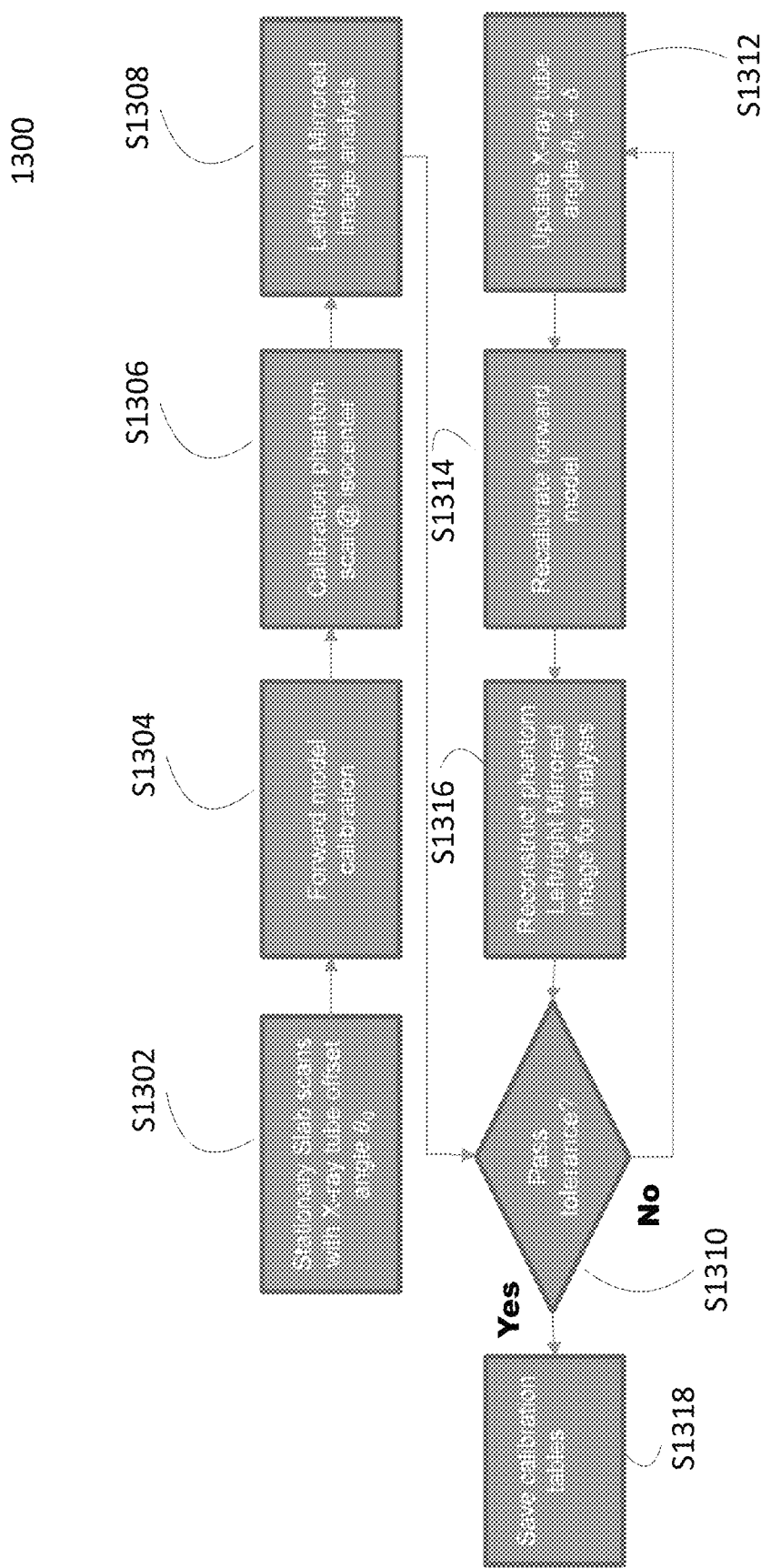
FIG. 13 is a flowchart showing an exemplary method of performing self-calibration.

FIG. 13 shows one embodiment of a self-calibration method 1300 illustrating self-calibrating of an X-ray tube/detector position with respect to a slab coordinate system for stationary slab scans by using a mirrored image from at least one phantom, to improve the calibration accuracy.

In step S1302, a slab of known material is first positioned such that path lengths are known and controlled assuming that the X-ray tube is parked at a center position with a zero angular offset. In an embodiment, the slab is a flat slab with a known thickness. One or more stationary X-ray tubes positioned on the CT gantry scan the slab to acquire calibration information data based on the stationary scans. The calibration information data of the stationary scans includes measuring the slab thickness and calculating a ground truth slab path length based on the scan performed at the center position with the zero angular offset by on one or more stationary X-ray tubes parked at a fixed location operating at various kVp and flux levels. In one embodiment, since at this step, the offset associated with an actual X-ray tube angle is not known, the stationary scans are performed assuming a zero angular offset when the calibration information data is acquired.

In step S1304, a forward PCD measurement model is calibrated based on the acquired calibration information data assuming the offset $\tau$ associated with the X-ray tube angle is $\tau=0$ and based on the one or more known materials of the slab as explained earlier with reference to FIG. 6 and equations 1-7. Further, the previously calculated ground truth slab path length during the stationary slab scan in S1302 is utilized in the forward PCD measurement model to generate an initial calibration table.

In step S1306, a rotational scan is performed on a calibration phantom, e.g. a cylindrical uniform phantom located at an isocentre. For the rotational scan of the calibration phantom, the same kVp value(s) is/are selected as that selected for the stationary slab scans in S1302 so that the previously calibrated forward PCD measurement model resulting from the stationary slab scan is synchronized with the rotational scan. Further, the mA values used during the rotational scan are within the range of the mA setting used during the stationary slab scan. The rotational scan is performed with the initial estimate of the X-ray tube angle at an offset of $\tau=0$ degrees associated with the one or more stationary X-ray tubes positioned on the CT gantry for a plurality of detector channels using the forward calibration model calculated in S1304 to generate sinogram data 1402. The sinogram data 1402 is explained with reference to FIG. 14. The calibration table of the forward PCD measurement model generated in step S1304 is utilized to estimate a path length of the calibration phantom through material decomposition process explained previously in FIG. 6. This estimated path length is utilized to calibrate or generate the sinogram data 1402, associated with the phantom for detector channels (e.g. channel 1-channel N included in an X-ray detector).

In another embodiment, the rotational scan may be performed with the initial estimate of the X-ray tube angle at an offset of $\tau=0$ degrees associated with the one or more stationary X-ray tubes positioned on the CT gantry for a subset of the plurality of detector channels using the forward calibration model calculated in S1304 to generate sinogram data 1402. The subset of the plurality of detector channels are symmetric around the isocenter of the cylindrical uniform phantom. In a difference image, the center ROI is most sensitive to tube angle offset in calibration data, and it is possible to use only the center channels as long as the FOV is large enough for the cylindrical phantom used.

In step S1308, with reference to FIG. 14, the sinogram data 1402 is split into a left half 1404 and a right half 1406 across the line of symmetry 1402a, such that the left-half 1404 corresponds to a curve of detector channels 1-channel N/2−1 and the right-half 1406 corresponds to a curve of detector channels N/2−channel N. Next, the left half 1404 of the sinogram data 1402 is mirror-copied to generate a left mirrored projection 1408 also referred to as left mirrored sinogram data 1408 or left mirror-copied sinogram data. Further, the right half 1406 of the sinogram data 1402 is mirror-copied to generate a right mirrored projection 1410 also referred to as right mirrored sinogram data 1410 or right mirror-copied sinogram. Accordingly, the left mirrored projection 1408 and the right mirrored projection 1410 are mirrored sinograms generated from the sinogram data 1402. Further, the left mirrored projection 1408 is reconstructed to generate a left mirrored image 1412 and the right mirrored projection 1410 is reconstructed to generate a right mirrored image 1414.

In step S1310, an analysis is performed on at least one of the left mirrored image 1412 and the right mirrored image 1414 to determine at least one parameter (e.g., a difference in a magnitude of Hounsfield unit (HU) bias) corresponding with the left mirrored image 1412 and the right mirrored image 1414. (Furthermore, while the discussion herein focuses on using the entirety of at least one of the left and right mirrored images, sub portions of those images can be used in alternate embodiments, such as a band extending left-to-right across the image(s), especially at a center of the image(s).) It is then determined if the at least one parameter exceeds a previously stored threshold value, e.g., whether a difference in magnitude of the HU bias associated with the left mirrored image 1412 and the right mirrored image 1414 exceeds a previously stored threshold value. The threshold value is an indicator of a pass tolerance associated with at least one of the reconstructed left and right images. In an embodiment, the previously stored threshold value is 0.5HU, and when the difference in magnitude of the HU bias associated with the left mirrored image 1412 and the right mirrored image 1414 is less than 0.5HU, then the pass tolerance associated with the reconstructed left image and the reconstructed right image is satisfied. Further, when the difference in magnitude of the HU bias associated with the left mirrored image 1412 and the right mirrored image 1414 is more than 0.5HU, then the pass tolerance associated with the reconstructed left image and the reconstructed right image is not satisfied.

In another embodiment, in step S1310, the analysis may be performed on only the left mirrored image 1412 to determine at least one parameter (e.g., a magnitude of HU bias) corresponding with the left mirrored image 1412. It is then determined if the at least one parameter exceeds a previously stored threshold value, e.g., whether a magnitude of the HU bias associated with the left mirrored image 1412 exceeds a previously stored threshold value. The threshold value is an indicator of a pass tolerance associated the reconstructed left image. In an embodiment, the previously stored threshold value is 0.5HU, and when the magnitude of the HU bias associated with the left mirrored image 1412 is less than 0.5HU, then the pass tolerance associated with the reconstructed left image is satisfied. Further, when the magnitude of the HU bias associated with the left mirrored image 1412 is more than 0.5HU, then the pass tolerance associated with the reconstructed left image is not satisfied.

In another embodiment, in step S1310, the analysis is performed on the right mirrored image 1414 to determine at least one parameter (e.g., a magnitude of HU bias) corresponding with the right mirrored image 1414. It is then determined if the at least one parameter exceeds a previously stored threshold value, e.g., whether a magnitude of the HU bias associated with the right mirrored image 1414 exceeds a previously stored threshold value. The threshold value is an indicator of a pass tolerance associated the reconstructed right image. In an embodiment, the previously stored threshold value is 0.8HU, and when the magnitude of the HU bias associated with the right mirrored image 1414 is less than 0.8HU, then the pass tolerance associated with the reconstructed right image is satisfied. Further, when the magnitude of the HU bias associated with the right mirrored image 1414 is more than 0.8HU, then the pass tolerance associated with the reconstructed right image is not satisfied.

In one embodiment, when the parameter is less than the threshold (e.g., when the difference in magnitude of the HU bias does not exceed the previously stored threshold value) then it is determined that there is a sufficiently small estimated difference between an estimated X-ray tube angle and the actual X-ray tube angle of the slab calibration measurements. Then the method takes the "YES" branch and proceeds to step S1318.

On the other hand, when step S1310 determines that at least one image does not pass the tolerance test (e.g., the difference in magnitude of the HU bias does exceed the previously stored threshold value) then it is determined that there is an unacceptably high offset between the estimated X-ray tube angle (initially assumed to be an offset of $\tau=0$) and the actual X-ray tube angle during the slab calibration measurements. Accordingly, it is determined that the initial estimate of X-ray tube angle with an offset of $\tau=0$ is to be updated to reduce the determined parameter (e.g., difference in magnitude of the HU bias) and the method takes the "NO" branch and flows to step S1312. In step S1312, the initial estimate of the X-ray tube angle (with an initial estimate $\tau=0$) is updated to a new offset estimate of $\tau=0+\delta$, where $\delta$ is an offset amount (e.g., 5 degrees). Thus, the updated estimate of the X-ray tube angle is at an offset of $\tau=5$ degrees. The ground truth slab path length that had been calculated at i=0 during the stationary scan is now re-calculated based on the updated estimate of the X-ray tube angle at an offset of $\tau=5$ degrees.

In step S1314, the forward PCD measurement model is re-calibrated based on the updated estimate of the X-ray tube angle at the new estimate (at an offset of $\tau=5$ degrees, the known material of the flat slabs, and the measured slab thicknesses. Further, the re-calculated ground truth slab path lengths are utilized in the forward PCD measurement model to generate an updated calibration table. The calibration table generated in step S1314 is utilized to re-estimate path lengths through the phantom through a material decomposition process explained previously with respect to FIG. 6. The re-estimated path length is utilized to re-calibrate the sinogram 1402 associated with the phantom for detector channels (e.g. channel 1-channel N) included in an X-ray detector.

In step S1316, based on the re-calibrated sinogram 1402, at least one of an updated left mirrored image and an updated right mirrored image is reconstructed. The method of reconstructing the updated left mirrored image and/or the updated right image is substantially similar to the method of reconstructing the left mirrored image 1412 and right mirrored image 1414 from sinogram 1402 as explained previously with reference to FIG. 14 in step S1308. Upon reconstructing the updated left mirrored image and/or the updated right image the method loops back to step S1310.

Now in step S1310, an analysis is performed again of at least one of the updated left mirrored image and the updated right mirrored image to determine if the calculated parameter (e.g., a difference in a magnitude of HU bias) now passes its tolerance test. For example, a comparison is made to determine if the difference in magnitude of the HU bias exceeds the previously stored threshold value. Accordingly, when the comparison indicates that the difference in magnitude of the HU bias does exceed the previously stored threshold value then it is determined that there is still an unacceptably high offset between the updated estimate of the X-ray tube angle at an offset of τ=5 degrees and the actual X-ray tube angle during the calibration measurements. Thus, it is determined that the current updated estimate of offset angle 0+δ is to be updated again to reduce the determined difference in magnitude of the HU bias and the method takes the "NO" branch and flows to step S1312.

However, back in step S1310 when the difference in magnitude of the HU bias does not exceed the previously stored threshold value then it is determined that the actual X-ray tube angle has been estimated sufficiently closely during the calibration measurements. Then the method takes the "YES" branch and proceeds to step S1318.

In step S1318, the calibration table associated with the reconstructed left image and the reconstructed right image that satisfies a pass is stored in a memory device or a storage device associated with a CT.

In an embodiment, a calibration phantom may include any other type of phantom having sufficiently known characteristics that can be modeled to find the actual X-ray tube angle. An exemplary size of this phantom can be in the range of 20 cm-40 cm in diameter, and an exemplary material of the phantom can be water, although other materials are possible with similar or different densities and/or attenuation properties. For the rotational scan of the phantom, the same kVp is chosen as during the slab scan, as a result the calibrated forward model is properly applied. The mA setting for scanning the uniform phantom is within the range of the mA setting used during scanning the slabs. The pathlength sinogram of the phantom is estimated with an initially calibrated PCD forward model, which uses an initial best estimate of the X-ray tube angle to calculate the slab's path length during the slab scans. The phantom scan sinogram is split into left and right half from the centre of the detector channel and further the split sinogram is left/right mirrored to generate the left-mirrored and right-mirrored sinograms and the left-mirrored and right-mirrored images are generated using standard filtered back projection (FBP). The centre of the mirrored images are most sensitive to the offset in the X-ray tube angle, and hence the centre of the mirrored images are used to determine the offset associated with the X-ray tube angle with best accuracy.

In another embodiment, any other type of calibration phantom may also be utilized to perform operations of method 1300. In an embodiment the operations of method 1300 are performed when the phantom is slightly off-center. In another embodiment the calibration phantom is placed in the vicinity of the CT system isocentre for such scans.

Figure 15A:
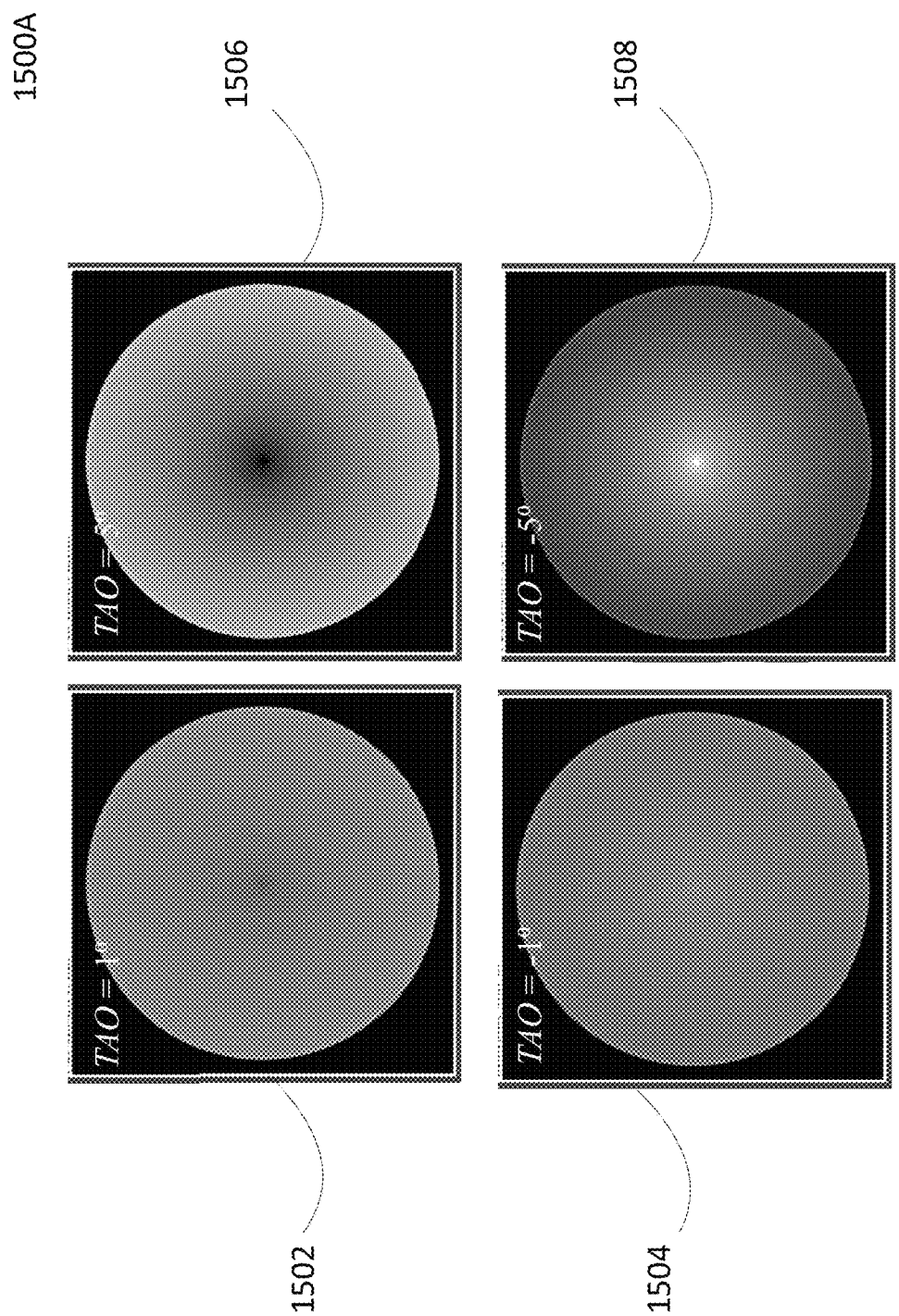
FIG. 15A shows a series of images corresponding to left mirrored images corresponding to different offset angles.

FIG. 15A illustrates a set of four images 1500A of reconstructed left-mirrored image 1412 at different estimated offsets i associated with the X-ray tube angle in the calibration scans. Images 1502, 1504, 1506, and 1508 are reconstructed left-mirrored images resulting from an estimated X-ray tube angle of τ=1 degree, τ=−1 degree, τ=5 degrees, and τ=−5 degrees, respectively. The images 1502, 1504, 1506, and 1508 show maximum HU bias in the phantom center, and also a gradual bias change in the radial direction. Either or both of those conditions can be used to determine if the estimated X-ray tube angle is correct.

Figure 15B:
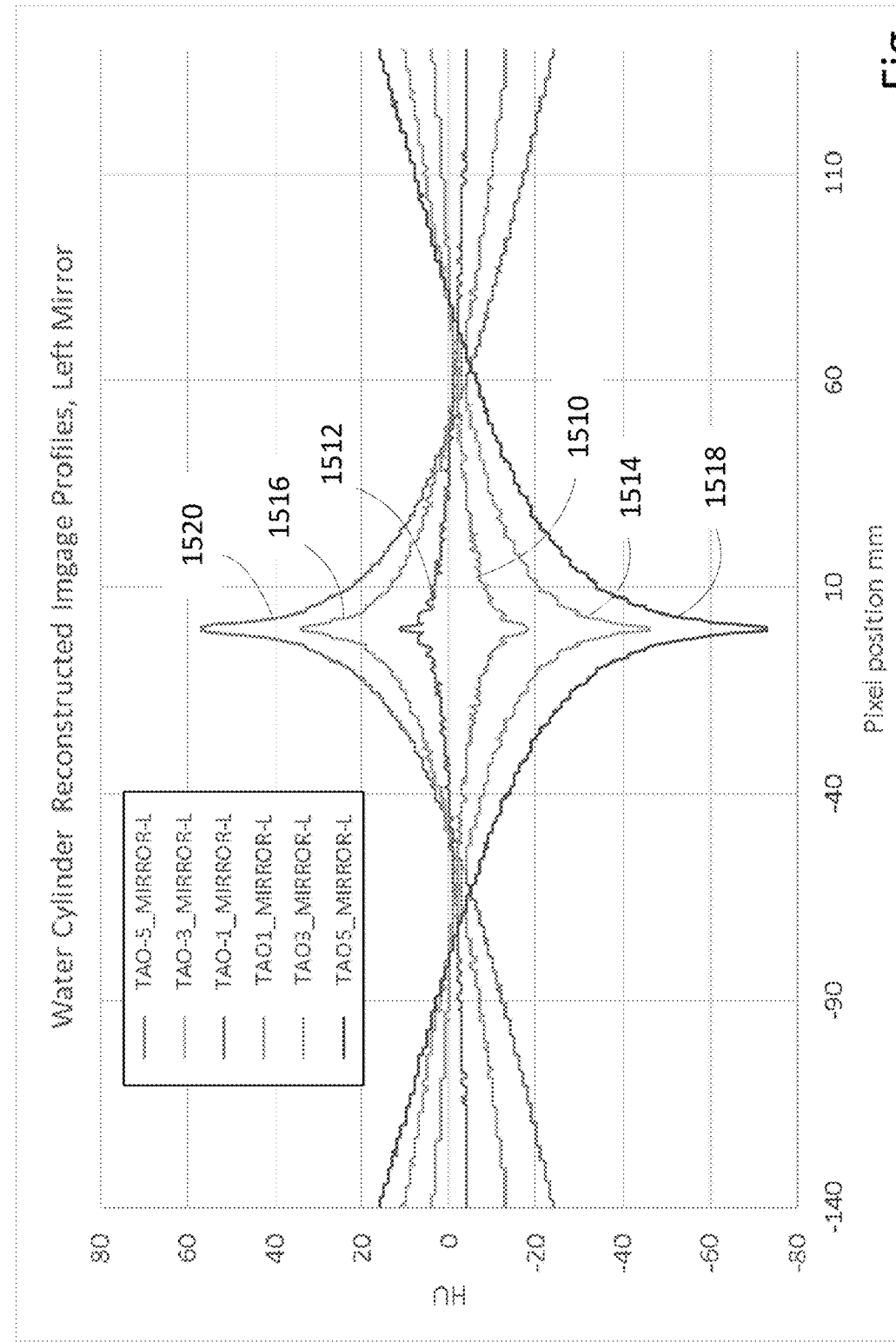
FIG. 15B shows a graph of a series of left mirrored images corresponding to different offset angles.

FIG. 15B illustrates a graph 1500B of magnitude of HU bias associated with the left-mirrored image 1412 (FIG. 14) at various offsets τ associated with the X-ray tube angle during the slab calibration measurements. Graph 1500B shows curves 1510, 1512, 1514, 1516, 1518, and 1520 that represent the magnitude of HU bias associated with left-mirrored images resulting from an estimated X-ray tube angle of τ=1 degree, τ=−1 degree, τ=3 degrees, τ=−3 degrees, τ=5 degrees, and τ=−5 degrees, respectively. Curves 1510, 1512, 1518, and 1520 correspond to the left mirrored images 1502, 1504, 1506, and 1508, respectively, of FIG. 15A.

Figure 16A:
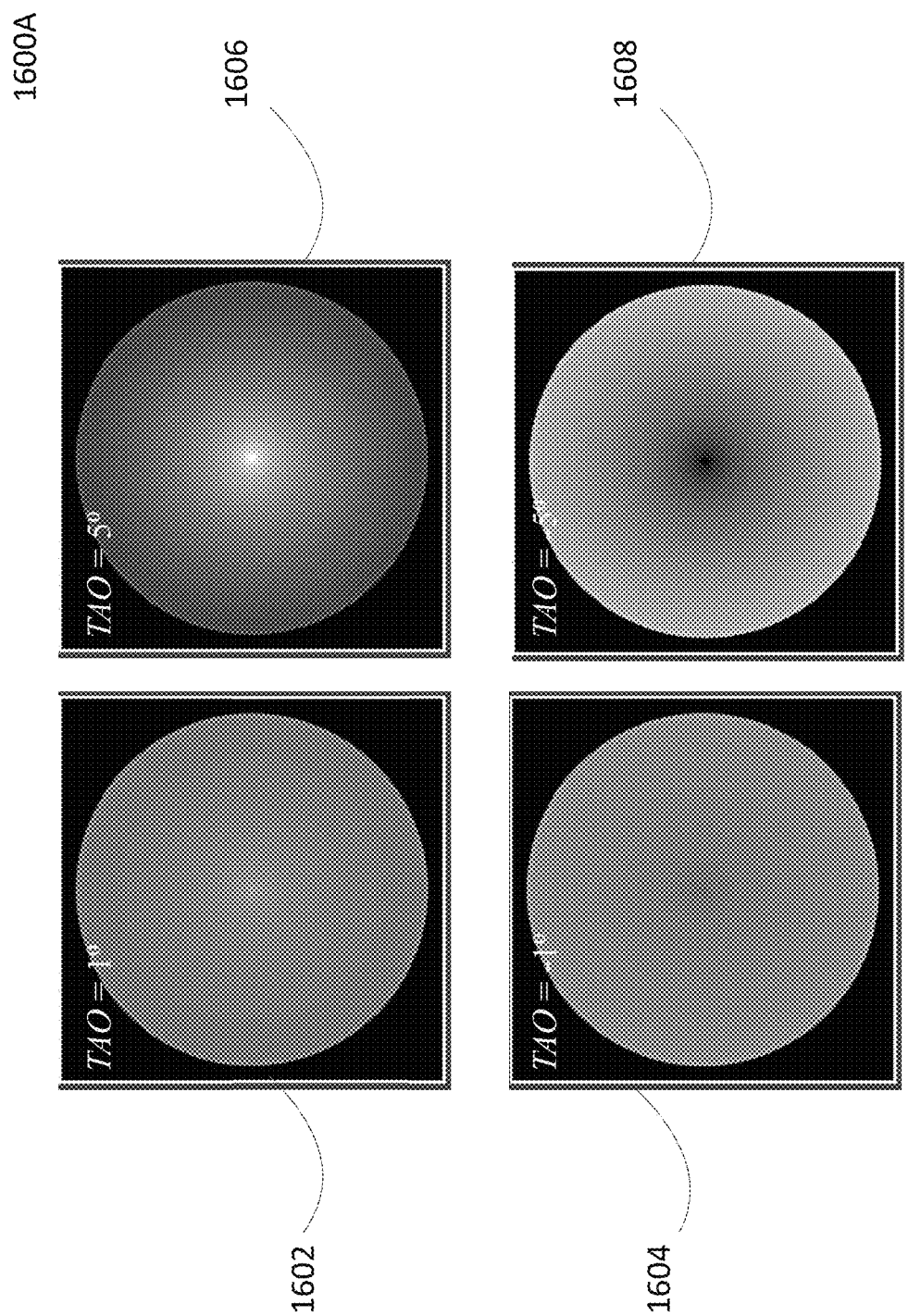
FIG. 16A shows a series of images corresponding to right mirrored images corresponding to different offset angles.

FIG. 16A illustrates a set of four images 1600A of reconstructed right-mirrored image 1412 at different estimated offsets i associated with the X-ray tube angle in the calibration scans. Images 1602, 1604, 1606, and 1608 are reconstructed right-mirrored images resulting from an estimated X-ray tube angle of τ=1 degree, τ=−1 degree, τ=5 degrees, and τ=−5 degrees, respectively. The images 1602, 1604, 1606, and 1608 show maximum HU bias in the phantom center, and also a gradual bias change in the radial direction. Either or both of those conditions can be used to determine if the estimated X-ray tube angle is correct.

Figure 16B:
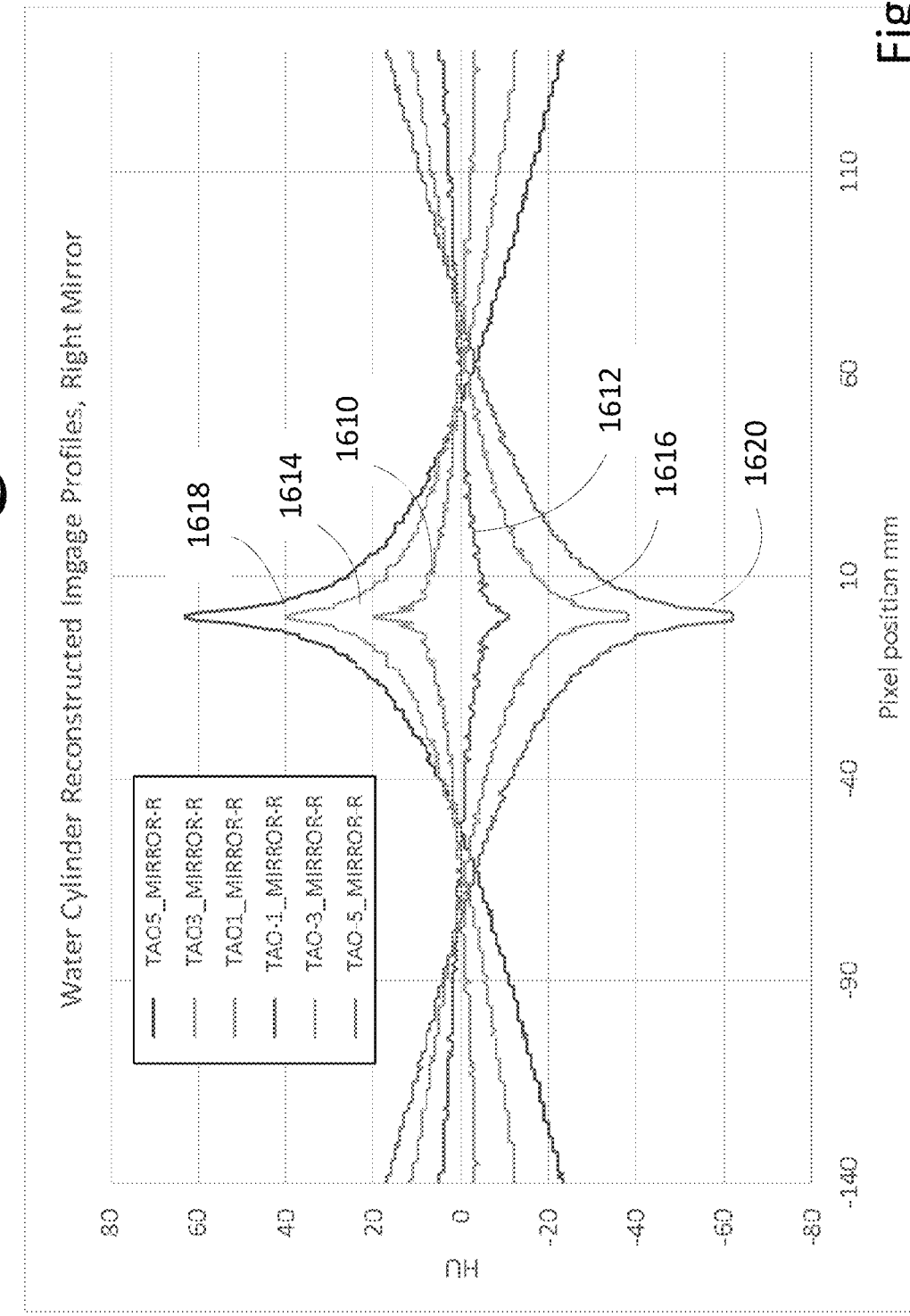
FIG. 16B shows a graph of a series of right mirrored images corresponding to different offset angles.

FIG. 16B illustrates a graph 1600B of magnitude of HU bias associated with the right-mirrored image 1412 (FIG. 14) at various offsets τ associated with the X-ray tube angle during the slab calibration measurements. Graph 1600B shows curves 1610, 1612, 1614, 1616, 1618, and 1620 that represent the magnitude of HU bias associated with right-mirrored images resulting from an estimated X-ray tube angle of τ=1 degree, τ=−1 degree, τ=3 degrees, τ=−3 degrees, τ=5 degrees, and τ=−5 degrees, respectively. Curves 1610, 1612, 1618, and 1620 correspond to the right-mirrored images 1602, 1604, 1606, and 1608, respectively, of FIG. 16A.

Figure 16C:
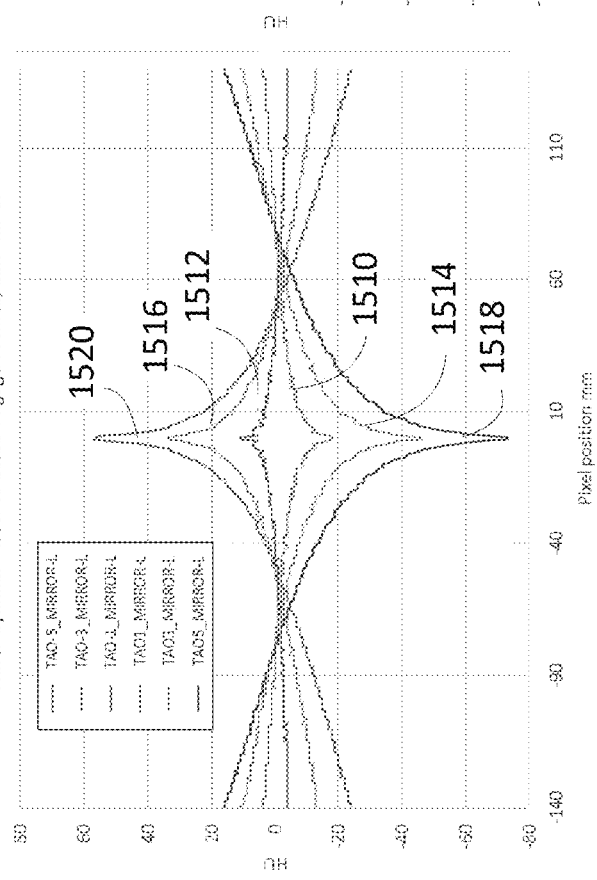
FIG. 16C shows a side by side comparison of FIG. 15B and FIG. 16B illustrating a graph of a series of left mirrored images and a series of right mirrored images corresponding to different offset angles respectively.

FIG. 16C illustrates the graph 1500B of FIG. 15B and the graph 1600B of FIG. 16B for side by side comparison purposes. The magnitude of HU bias of 1500B and 1600B are analysed to determine differences between the biases. The greater the difference between the magnitude of HU bias of the left-mirrored image and the right-mirrored image, the greater is the offset angle. The true offset angle is identified when the difference between the magnitude of HU bias of left-mirrored image and right-mirrored image is the lowest or completely eliminated. Accordingly, based on the comparison of the magnitude of HU bias of left-mirrored images represented by the graph 1500B, the magnitude of HU bias of the right-mirrored images represented by the graph 1600B have similar magnitude but are in an opposite direction with the same tube offset angle. As illustrated by the graph 1500B, when the actual X-ray tube angle is offset by τ=−1 degree represented by curve 1512, an estimated offset of τ=−1 degree is identified as the lowest value of offset. Further, as illustrated by the graph 1600B when the actual X-ray tube angle is offset by τ=−1 degree represented by curve 1612, the angle of τ=−1 degree is identified as the lowest value of offset.

Figures 17A, 17B:
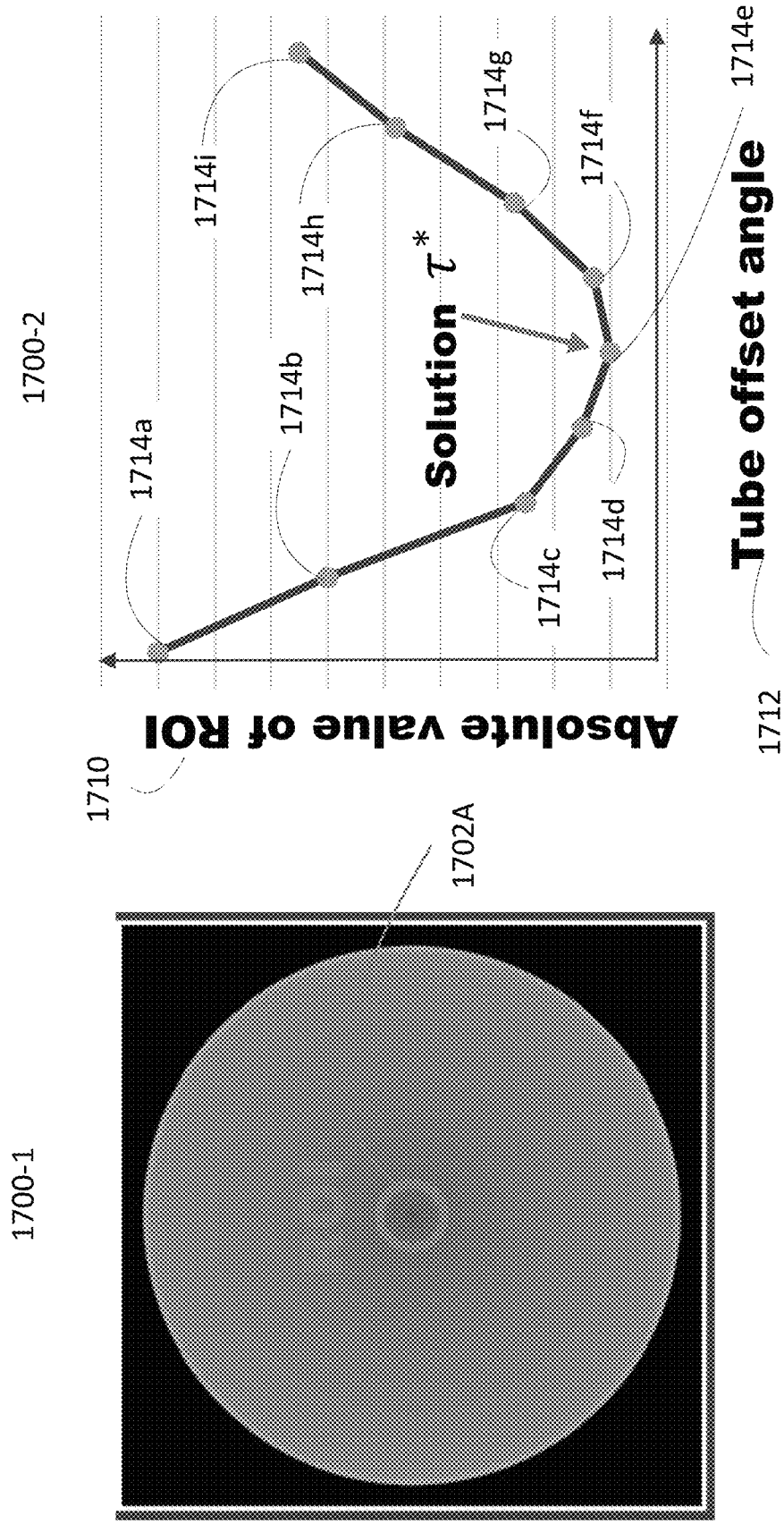
FIG. 17A shows an exemplary mirrored image having a circular region of interest (ROI) used to estimate an X-ray tube offset angle.
FIG. 17B is a graph showing a correlation between X-ray tube offset angle and an absolute value of a correlation factor that is used to identify an X-ray offset angle.

FIG. 17A illustrates a phantom image 1700-1 for which a circular region of interest (ROI) 1702A is analysed to determine if an offset τ for an X-ray tube angle associated with the image satisfies a pass tolerance. Phantom image 1700-1 may be, with reference to FIG. 14, a left mirrored image 1412 or a right mirrored image 1414. Alternatively, a difference image may be used that is a difference between an image reconstructed directly from left mirror projection sinogram 1408 and an image reconstructed directly from the right mirror projection sinogram 1410.

A calibration parameter corresponding with ROI 1702A is calculated based on performing the operations of FIG. 13 to generate at least one of a left mirrored image and a right mirrored image (as explained earlier with reference to FIG. 14) for ROI 1702A at different X-ray tube angles for each pixel within the ROI 1702A. Further, the calibration parameter (e.g., the magnitude of the HU bias) associated with the ROI 1702A is determined for each of several different X-ray tube angles based on at least one of the left mirrored image and the right mirrored image. The magnitude of HU bias (acting as an exemplary calibration parameter) associated with the ROI 1702A associated with each of several different offset angles for the X-ray tube angle are plotted on the graph 1700-2 of FIG. 17B.

Figure 17C:
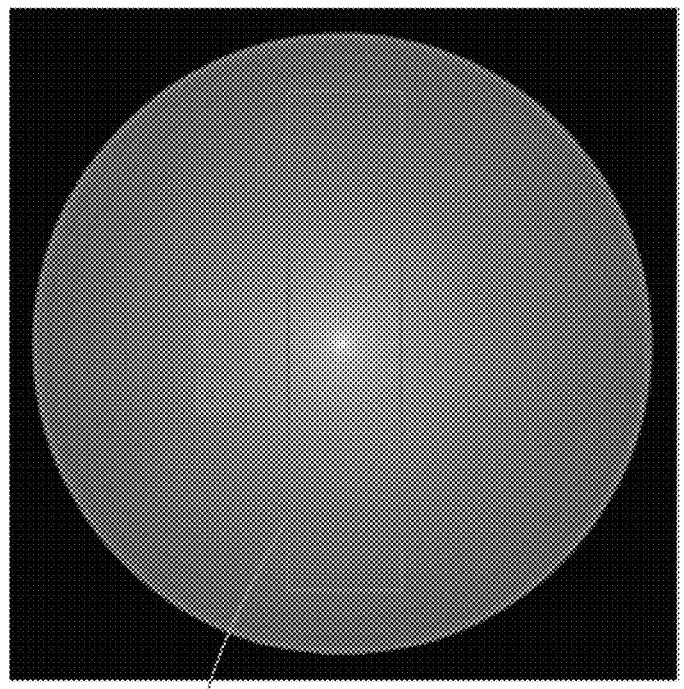
FIG. 17C shows an exemplary mirrored image having a rectangular ROI used to estimate an X-ray tube offset angle.

The graph 1700-2 illustrates a correlation between an exemplary set of absolute mean values of ROI 1702A (on axis 1710) and a set of exemplary tube offset angles (on axis 1712). As illustrated, point 1714e has a minimum value and represents an optimized value $\tau^*$ at an X-ray tube angle that is close to zero. Other points 1714f and 1714d, corresponding to X-ray tube angles on either side of 1714e, are slightly higher, and the remaining points 1714c, 1714g, 1714h, 1714b, 1714i, and 1714a are even worse as they are farther away from the optimized value $\tau^*$. In one embodiment of an iterative method for determining an X-ray tube angle to be used, the method determines a minimum value of the calculated absolute mean values of the ROI 1702A as the calibration parameter. As would be evident to those of ordinary skill in the art, other shapes than the circular ROI can be used, such as a right-to-left ROI band 1702C centered at the center top-to-bottom and right-to-left in the reconstructed image 1700-3 as shown in FIG. 17C.

During the iterative process, the method can either (1) stop searching for the X-ray tube angle once a calibration parameter is found that is below a threshold or (2) continue to determine additional calibration parameters across a range of estimated X-ray tube angles and then select an angle for which the calibration parameter is a local peak (e.g., maximum or minimum). For example, if the estimated X-ray tube angle is initially selected at an angle corresponding to point 1714a and increased for each subsequent check, then in the first embodiment, it is possible that point 1714d would have been below a specified threshold such that the process would terminate. However, in the second embodiment, the process would continue until the angle corresponding to step 1714i. The angle corresponding to point 1714e would then be selected as the minimum peak. Alternatively, using a heuristic with the continuing process, it also is possible to stop after calculating the calibration parameter for point 1714f because, having started at 1714a, point 1714e is already a better result than 1714e. Thus, reconstruction images would not have to be generated for angles greater than that corresponding to 1714f.

In yet another optimization method, the method initially selects an estimated X-ray tube angle to be 0 and then performs checks of the calibration parameter at points corresponding to angles on each side of 0 (e.g., −1 and 1) and continuing on through a number of angles (e.g., using sequence −1, −2, −3, −4, etc. on a first side and sequence 1, 2, 3, 4, etc. on a second side). When a calibration parameter on either side becomes worse than a previous calibration parameter on that side, searching can stop on that side. The method can then determine points in between the current best choices on each side (e.g., by halving the distance between the entries on a side for a number of halving operation) until a peak value is found.

While the above discussion has been provided with respect to determining a calibration parameter based on a reconstructed image generated by reconstructing mirror-copied sinogram data, it also is possible to determine the calibration parameter directly from the sinogram data when the phantom is placed at the isocenter of the channels. In one such embodiment, the system and method calculates a uniformity measure (e.g., a difference) between two symmetrical sets of detector channels (e.g., between the left and right half of the detector channels). When the calculated uniformity measure meets a sinogram-data specific threshold (or alternatively is the best uniformity measure among those uniformity measures meeting the threshold), then the corresponding x-ray tube offset angle has been determined.

Figure 18:
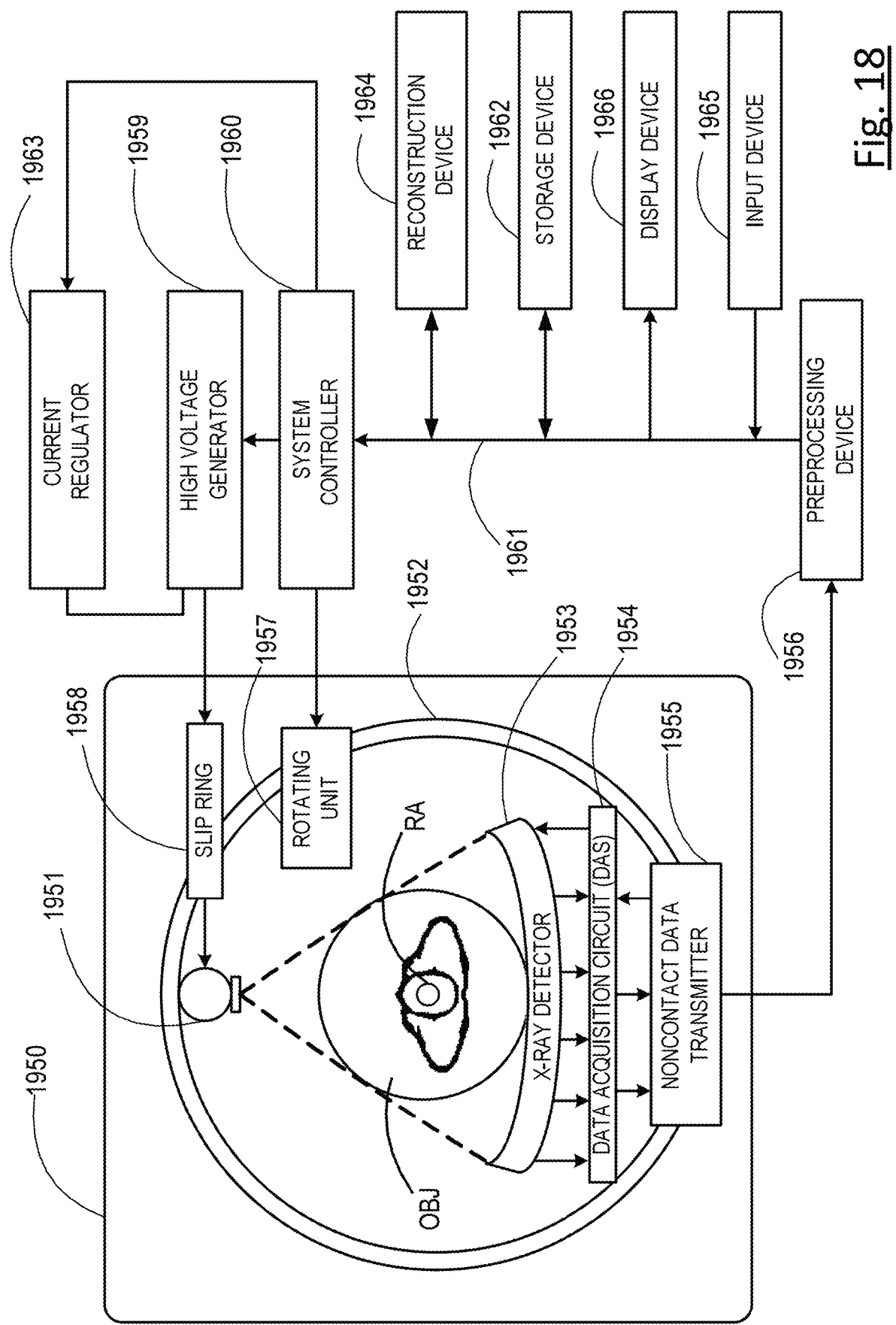
FIG. 18 shows a CT scanner system that can incorporate the techniques disclosed herein.

It can be appreciated that, in one embodiment, the above mentioned techniques can be applied to a CT apparatus or scanner. FIG. 18 illustrates an implementation of a horizontal radiography gantry included in a CT apparatus or scanner. As shown in FIG. 18, a radiography gantry 1950 (illustrated from a side view) includes an X-ray tube 1951, an annular frame 1952, and a multi-row or two-dimensional-array-type X-ray detector 1953. The X-ray tube 1951 and X-ray detector 1953 are diametrically mounted across an object OBJ (e.g., a patient) on the annular frame 1952, which is rotatably supported around a rotation axis RA. A rotating unit 1157 rotates the annular frame 1952 at a high speed, such as 0.4 sec/rotation, while the object OBJ (e.g., a patient) is being moved along the axis RA into or out of the illustrated page.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 1959 that generates a tube voltage applied to the X-ray tube 1951 through a slip ring 1958 so that the X-ray tube 1951 generates X-rays. An X-ray detector 1953 is located at an opposite side from the X-ray tube 1951 across the object OBJ (e.g., a patient) for detecting the emitted X-rays that have transmitted through the object OBJ (e.g., a patient). The X-ray detector 1953 further includes individual detector elements or units and may be a photon-counting detector. In the fourth-generation geometry system, the X-ray detector 1953 may be one of a plurality of detectors arranged around the object OBJ (e.g., a patient) in a 360° arrangement.

The CT apparatus further includes other devices for processing the detected signals from the X-ray detector 1953. A data acquisition circuit or a Data Acquisition System (DAS) 1954 converts a signal output from the X-ray detector 1953 for each channel into a voltage signal, amplifies he signal, and further converts the signal into a digital signal. The X-ray detector 1953 and the DAS 1954 are configured to handle a predetermined total number of projections per rotation (TPPR).

The above-described data is sent to a preprocessing device 1956, which is housed in a console outside the radiography gantry 1950 through a non-contact data transmitter 1955. The preprocessing device 1956 performs certain corrections, such as sensitivity correction, on the raw data. A memory 1962 stores the resultant data, which is also called projection data at a stage immediately before reconstruction processing. The memory 1962 is connected to a system controller 1960 through a data/control bus 1961, together with a reconstruction device 1964, input device 1965, and display 1966. The system controller 1960 controls a current regulator 1963 that limits the current to a level sufficient for driving the CT system. In an embodiment, the system controller 1960 implements optimized scan acquisition parameters, as described above. The reconstruction device 1964 can include circuitry configured to perform the above mentioned techniques, such as method 600 and 1300.

The method and system described herein can be implemented in a number of technologies but generally relate to imaging devices and/or processing circuitry for performing the techniques described herein. In one embodiment, the processing circuitry is implemented as one of or as a combination of: an application specific integrated circuit (ASIC), a field programmable gate array (FPGA), a generic array of logic (GAL), a programmable array of logic (PAL), circuitry for allowing one-time programmability of logic gates (e.g., using fuses) or reprogrammable logic gates. Furthermore, the processing circuitry can include computer processor circuitry having embedded and/or external non-volatile computer readable memory (e.g., RAM, SRAM, FRAM, PROM, EPROM, and/or EEPROM) that stores computer instructions (binary executable instructions and/or interpreted computer instructions) for controlling the computer processor to perform the processes described herein. The computer processor circuitry may implement a single processor or multiprocessors, each supporting a single thread or multiple threads and each having a single core or multiple cores.

Embodiments of the present disclosure may also be as set forth in the following parentheticals.

(1) A calibration method comprising: acquiring sinogram data by scanning a symmetrical phantom using a plurality of detector channels; generating mirror-copied sinogram data by mirror-copying at least one of first sinogram data and second sinogram data of the acquired sinogram data, wherein the first sinogram data and the second sinogram data are generated by dividing the sinogram data at a center detector channel of the plurality of detector channels; outputting a first reconstructed image by reconstructing the mirror-copied sinogram data; and determining a calibration parameter based on the first reconstructed image.

(2) The method as claimed in claim 1, further comprising: acquiring calibration information data by scanning a slab using the plurality of detector channels, and calibrating a forward calibration model based on the acquired calibration information data.

(3) The method as claimed in claim 1, further comprising: estimating an X-ray tube angle offset amount based on the first reconstructed image; and determining the calibration parameter based on the estimated X-ray tube angle offset and the first reconstructed image.

(4) The method of claim 3, further comprising: (a) updating, based on the determined calibration parameter, the estimated X-ray tube angle by an offset amount; (b) generating updated sinogram data using the updated estimated X-ray tube angle; (c) generating updated mirror-copied sinogram data by mirror-copying at least one of first sinogram data and second sinogram data of the updated sinogram data, wherein the first sinogram data and the second sinogram data of the updated sinogram data are generated by dividing the updated sinogram data at the center detector channel of the plurality of detector channels; (d) outputting a second reconstructed image by reconstructing the updated mirror-copied sinogram data; and (e) determining an updated calibration parameter based on the third reconstructed image.

(5) The method of claim 4, further comprising: repeating steps (a)-(e) to determine an estimated X-ray tube angle for which the calibration parameter meets a specified threshold.

(6) The method of claim 4, further comprising: repeating steps (a)-(e) to determine an estimated X-ray tube angle for which the calibration parameter is a peak among the determined calibration parameters.

(7) The method of claim 1, wherein the symmetrical phantom is a cylindrical phantom.

(8) The method of claim 1, wherein the generating mirror-copied sinogram data comprises generating mirror-copied sinogram data by mirror-copying the first sinogram data and the second sinogram data of the acquired sinogram data; wherein outputting the first reconstructed image comprises outputting the first reconstructed image and a second reconstructed image by reconstructing the first and second mirror-copied sinogram data, respectively; and wherein determining the calibration parameter based on the first reconstructed image comprises determining the calibration parameter based on the first and second reconstructed images by determining an amount of correlation between at least a portion of the first and second reconstructed images.

(9) The method of claim 8, wherein the amount of correlation comprises an amount of uniformity in at least a portion of the first and second reconstructed images.

(10) The method of claim 2, further comprising: scanning the slab with an X-ray tube located at known locations on an X-ray scanner system, wherein the slab has a known linear attenuation coefficient and a known pathlength; generating material decomposition data based on the scanning of the slab; generating air calibration data based on an air scan using the X-ray tube at a rotation speed; and calibrating the forward model for the X-ray scanner system based at least on the material decomposition data and the air scan.

(11) An imaging apparatus comprising: processing circuitry configured to: acquire sinogram data by scanning a symmetrical phantom using a plurality of detector channels; generate mirror-copied sinogram data by mirror-copying at least one of first sinogram data and second sinogram data of the acquired sinogram data, wherein the first sinogram data and the second sinogram data are generated by dividing the sinogram data at a center detector channel of the plurality of detector channels; output a first reconstructed image by reconstructing the mirror-copied sinogram data; and determine a calibration parameter based on the first reconstructed image.

(12) The apparatus as claimed in claim 11, wherein the processing circuitry is further configured to: acquire calibration information data by scanning a slab using the plurality of detector channels, and calibrate a forward calibration model based on the acquired calibration information data.

(13) The apparatus as claimed in claim 11, wherein the processing circuitry is further configured to: estimate an X-ray tube angle offset amount based on the first reconstructed image; and determine the calibration parameter based on the estimated X-ray tube angle offset and the first reconstructed image.

(14) The apparatus as claimed in claim 13, wherein the processing circuitry is further configured to: (a) update, based on the determined calibration parameter, the estimated X-ray tube angle by an offset amount; (b) generate updated sinogram data using the updated estimated X-ray tube angle; (c) generate updated mirror-copied sinogram data by mirror-copying at least one of first sinogram data and second sinogram data of the updated sinogram data, wherein the first sinogram data and the second sinogram data of the updated sinogram data are generated by dividing the updated sinogram data at the center detector channel of the plurality of detector channels; (d) output a second reconstructed image by reconstructing the updated mirror-copied sinogram data; and (e) determine an updated calibration parameter based on the third reconstructed image.

(15) The apparatus as claimed in claim 14, wherein the processing circuitry is further configured to: repeat functions (a)-(e) to determine an estimated X-ray tube angle for which the calibration parameter meets a specified threshold.

(16) The apparatus as claimed in claim 14, wherein the processing circuitry is further configured to: repeat functions (a)-(e) to determine an estimated X-ray tube angle for which the calibration parameter is a peak among the determined calibration parameters.

(17) The apparatus as claimed in claim 11, wherein the symmetrical phantom is a cylindrical phantom.

(18) The apparatus as claimed in claim 11, wherein the processing circuitry configured to generate mirror-copied sinogram data comprises processing circuitry configured to generate mirror-copied sinogram data by mirror-copying the first sinogram data and the second sinogram data of the acquired sinogram data; wherein the processing circuitry configured to output the first reconstructed image comprises processing circuitry configured to output the first reconstructed image and a second reconstructed image by reconstructing the first and second mirror-copied sinogram data, respectively; and wherein the processing circuitry configured to determine the calibration parameter based on the first reconstructed image comprises processing circuitry configured to determine the calibration parameter based on the first and second reconstructed images by determining an amount of correlation between at least a portion of the first and second reconstructed images.

(19) The apparatus as claimed in claim 18, wherein the amount of correlation comprises an amount of uniformity in at least a portion of the first and second reconstructed images.

(20) The apparatus as claimed in claim 12, wherein the processing circuitry is further configured to: scan the slab with an X-ray tube located at known locations on an X-ray scanner system, wherein the slab has a known linear attenuation coefficient and a known pathlength; generating material decomposition data based on the scanning of the slab; generate air calibration data based on an air scan using the X-ray tube at a rotation speed; and calibrate the forward model for the X-ray scanner system based at least on the material decomposition data and the air scan.

(21) A calibration method comprising: acquiring calibration information data by scanning a slab for a plurality of detector channels at an X-ray tube angle, calibrating a forward calibration model based on the acquired calibration information data at an estimated X-ray tube angle, wherein the estimated X-ray tube angle is an estimate of the X-ray tube angle, scanning a calibration phantom for the plurality of detector channels to generate sinogram data at the estimated X-ray tube angle based on the forward calibration model, generating mirrored sinogram data by mirroring a subset of the generated sinogram data on a first side of a line of symmetry, wherein the line of symmetry divides the plurality of detector channels, outputting a reconstructed image by reconstructing the mirrored sinogram data and the subset of the calibrated sinogram data that are separated by the line of symmetry, and determining a calibration parameter based on the correlation between a portion of the reconstructed image corresponding to the mirrored sonogram data and a portion of the reconstructed image corresponding to the subset of the calibrated sinogram data.

(22) The method of claim 21, further comprising: updating the estimated X-ray tube angle by an offset amount based on the determined calibration parameter, re-generating the sinogram data based on the updated estimated X-ray tube angle to generate a re-calibrated sinogram data, generating another mirrored sinogram data by mirroring a subset of the re-calibrated sinogram data on the first side of the line of symmetry, outputting another reconstructed image by reconstructing the another mirrored sinogram data and the subset of the re-calibrated sinogram data that are separated by the line of symmetry, and determining an updated calibration parameter based on the correlation between a portion of the reconstructed image corresponding to the another mirrored sonogram data and a portion of the reconstructed image corresponding to the subset of the re-calibrated sinogram data.

(23) The method of claim 21, further comprising: determining whether a difference between magnitude of the calibrated sinogram data and the mirrored sinogram data satisfies a threshold value, and storing the determined calibration parameter when the determination indicates that the difference between magnitude of the calibrated sinogram data and the mirrored sinogram data satisfies the threshold value.

(24) The method of claim 23, further comprising: updating the estimated X-ray tube angle by an offset amount when the determination indicates that the difference between magnitude of the calibrated sinogram data and the mirrored sinogram data does not satisfy the threshold value.

(25) The method of claim 21, further comprising: scanning the calibration phantom at an isocentre by an X-ray scanner system, wherein the calibration phantom is a circular uniform phantom.

(26) The method of claim 25, wherein the scanning of the calibration phantom is performed by a rotational scan around the circular uniform phantom, wherein the circular uniform phantom is a cylindrical phantom.

(27) The method of claim 21, further comprising: scanning the slab with an X-ray tube located at known locations on an X-ray scanner system, wherein the slab has a known linear attenuation coefficient and a known pathlength, generating material decomposition data based on the scanning of the slab, generating air calibration data based on an air scan using the X-ray tube at a rotation speed, and calibrating a forward model for the X-ray scanner system based at least on the material decomposition data and the air scan.

(28) The method of claim 27, wherein the material decomposition data includes a weighted bin response and a pulse pileup correction term.

(29) The method of claim 27, wherein the X-ray scanner system is a photon counting CT scanner system.

(30) The method of claim 27, wherein the X-ray scanner system is a 3rd generation photon counting CT scanner system.

(31) A system comprising processing circuitry configured to, acquire calibration information data by scanning a slab for a plurality of detector channels at an X-ray tube angle, calibrate a forward calibration model based on the acquired calibration information data at an estimated X-ray tube angle, wherein the estimated X-ray tube angle is an estimate of the X-ray tube angle, scan a calibration phantom for the plurality of detector channels to generate sinogram data at the estimated X-ray tube angle based on the forward calibration model, generate mirrored sinogram data by mirroring a subset of the generated sinogram data on a first side of a line of symmetry, wherein the line of symmetry divides the plurality of detector channels, output a reconstructed image by reconstructing the mirrored sinogram data and the subset of the calibrated sinogram data that are separated by the line of symmetry, and determine a calibration parameter based on the correlation between a portion of the reconstructed image corresponding to the mirrored sonogram data and a portion of the reconstructed image corresponding to the subset of the calibrated sinogram data.

(32) The system of claim 31, wherein the processing circuitry is configured to, update the estimated X-ray tube angle by an offset amount based on the determined calibration parameter, re-generate the sinogram data based on the updated estimated X-ray tube angle to generate a re-calibrated sinogram data, generate another mirrored sinogram data by mirroring a subset of the re-calibrated sinogram data on the first side of the line of symmetry, output another reconstructed image by reconstructing the another mirrored sinogram data and the subset of the re-calibrated sinogram data that are separated by the line of symmetry, and determine an updated calibration parameter based on the correlation between a portion of the reconstructed image corresponding to the another mirrored sonogram data and a portion of the reconstructed image corresponding to the subset of the re-calibrated sinogram data.

(33) The system of claim 11, wherein the processing circuitry is configured to, determine whether a difference between magnitude of the calibrated sinogram data and the mirrored sinogram data satisfies a threshold value; and store the determined calibration parameter when the determination indicates that the difference between magnitude of the calibrated sinogram data and the mirrored sinogram data satisfies the threshold value.

(34) The system of claim 33, wherein the processing circuitry is configured to, update the estimated X-ray tube angle by an offset amount when the determination indicates that the difference between magnitude of the calibrated sinogram data and the mirrored sinogram data does not satisfy the threshold value.

(35) The system of claim 31, wherein the processing circuitry is configured to, scan the calibration phantom at an isocentre by an X-ray scanner system, wherein the calibration phantom is a circular uniform phantom.

(36) The system of claim 35, wherein the scanning of the calibration phantom is performed by a rotational scan around the circular uniform phantom, wherein the circular uniform phantom is a cylindrical phantom.

(37) The system of claim 31, wherein the processing circuitry is configured to, scan the slab with an X-ray tube located at known locations on an X-ray scanner system, wherein the slab has a known linear attenuation coefficient and a known pathlength, generate material decomposition data based on the scanning of the slab, generate air calibration data based on an air scan using the X-ray tube at a rotation speed, and calibrate a forward model for the X-ray scanner system based at least on the material decomposition data and the air scan.

(38) The system of claim 37, wherein the material decomposition data includes a weighted bin response and a pulse pileup correction term.

(39) The system of claim 37, wherein the X-ray scanner system is a photon counting CT scanner system.

(40) The system of claim 37, wherein the X-ray scanner system is a 3rd generation photon counting CT scanner system.

Numerous modifications and variations of the embodiments presented herein are possible in light of the above teachings. It is therefore to be understood that within the scope of the claims, the disclosure may be practiced otherwise than as specifically described herein.

The invention claimed is:

1. A calibration method comprising:
acquiring sinogram data by scanning a symmetrical phantom using a plurality of detector channels;
generating mirror-copied sinogram data by mirror-copying at least one of first sinogram data and second sinogram data of the acquired sinogram data, wherein the first sinogram data and the second sinogram data are generated by dividing the sinogram data at a center detector channel of the plurality of detector channels;
outputting a first reconstructed image by reconstructing the mirror-copied sinogram data; and
determining a calibration parameter based on the first reconstructed image.

2. The method as claimed in claim 1, further comprising:
acquiring calibration information data by scanning a slab using the plurality of detector channels, and
calibrating a forward calibration model based on the acquired calibration information data.

3. The method as claimed in claim 1, further comprising:
estimating an X-ray tube angle offset amount based on the first reconstructed image; and
determining the calibration parameter based on the estimated X-ray tube angle offset and the first reconstructed image.

4. The method of claim 3, further comprising:
(a) updating, based on the determined calibration parameter, the estimated X-ray tube angle by an offset amount;
(b) generating updated sinogram data using the updated estimated X-ray tube angle;
(c) generating updated mirror-copied sinogram data by mirror-copying at least one of first sinogram data and second sinogram data of the updated sinogram data, wherein the first sinogram data and the second sinogram data of the updated sinogram data are generated by dividing the updated sinogram data at the center detector channel of the plurality of detector channels;
(d) outputting a second reconstructed image by reconstructing the updated mirror-copied sinogram data; and
(e) determining an updated calibration parameter based on the second reconstructed image.

5. The method of claim 4, further comprising:
repeating steps (a)-(e) to determine an estimated X-ray tube angle for which the calibration parameter meets a specified threshold.

6. The method of claim 4, further comprising:
repeating steps (a)-(e) to determine an estimated X-ray tube angle for which the calibration parameter is a peak among the determined calibration parameters.

7. The method of claim 1, wherein the symmetrical phantom is a cylindrical phantom.

8. The method of claim 1, wherein the generating mirror-copied sinogram data comprises generating mirror-copied sinogram data by mirror-copying the first sinogram data and the second sinogram data of the acquired sinogram data;
wherein outputting the first reconstructed image comprises outputting the first reconstructed image and a second reconstructed image by reconstructing the first and second mirror-copied sinogram data, respectively; and wherein determining the calibration parameter based on the first reconstructed image comprises determining the calibration parameter based on the first and second reconstructed images by determining an amount of correlation between at least a portion of the first and second reconstructed images.

9. The method of claim 8, wherein the amount of correlation comprises an amount of uniformity in at least a portion of the first and second reconstructed images.

10. The method of claim 2, further comprising:
scanning the slab with an X-ray tube located at known locations on an X-ray scanner system, wherein the slab has a known linear attenuation coefficient and a known pathlength;
generating material decomposition data based on the scanning of the slab;
generating air calibration data based on an air scan using the X-ray tube at a rotation speed; and
calibrating the forward model for the X-ray scanner system based at least on the material decomposition data and the air scan.

11. An imaging apparatus comprising:
processing circuitry configured to:
acquire sinogram data by scanning a symmetrical phantom using a plurality of detector channels;
generate mirror-copied sinogram data by mirror-copying at least one of first sinogram data and second sinogram data of the acquired sinogram data, wherein the first sinogram data and the second sinogram data are generated by dividing the sinogram data at a center detector channel of the plurality of detector channels;
output a first reconstructed image by reconstructing the mirror-copied sinogram data; and
determine a calibration parameter based on the first reconstructed image.

12. The apparatus as claimed in claim 11, wherein the processing circuitry is further configured to:
acquire calibration information data by scanning a slab using the plurality of detector channels, and
calibrate a forward calibration model based on the acquired calibration information data.

13. The apparatus as claimed in claim 11, wherein the processing circuitry is further configured to:
estimate an X-ray tube angle offset amount based on the first reconstructed image; and
determine the calibration parameter based on the estimated X-ray tube angle offset and the first reconstructed image.

14. The apparatus as claimed in claim 13, wherein the processing circuitry is further configured to:
(a) update, based on the determined calibration parameter, the estimated X-ray tube angle by an offset amount;
(b) generate updated sinogram data using the updated estimated X-ray tube angle;
(c) generate updated mirror-copied sinogram data by mirror-copying at least one of first sinogram data and second sinogram data of the updated sinogram data, wherein the first sinogram data and the second sinogram data of the updated sinogram data are generated by dividing the updated sinogram data at the center detector channel of the plurality of detector channels;
(d) output a second reconstructed image by reconstructing the updated mirror-copied sinogram data; and
(e) determine an updated calibration parameter based on the second reconstructed image.

15. The apparatus as claimed in claim 14, wherein the processing circuitry is further configured to:
repeat functions (a)-(e) to determine an estimated X-ray tube angle for which the calibration parameter meets a specified threshold.

16. The apparatus as claimed in claim 14, wherein the processing circuitry is further configured to:
repeat functions (a)-(e) to determine an estimated X-ray tube angle for which the calibration parameter is a peak among the determined calibration parameters.

17. The apparatus as claimed in claim 11, wherein the symmetrical phantom is a cylindrical phantom.

18. The apparatus as claimed in claim 11, wherein the processing circuitry configured to generate mirror-copied sinogram data comprises processing circuitry configured to generate mirror-copied sinogram data by mirror-copying the first sinogram data and the second sinogram data of the acquired sinogram data;
wherein the processing circuitry configured to output the first reconstructed image comprises processing circuitry configured to output the first reconstructed image and a second reconstructed image by reconstructing the first and second mirror-copied sinogram data, respectively; and
wherein the processing circuitry configured to determine the calibration parameter based on the first reconstructed image comprises processing circuitry configured to determine the calibration parameter based on the first and second reconstructed images by determining an amount of correlation between at least a portion of the first and second reconstructed images.

19. The apparatus as claimed in claim 18, wherein the amount of correlation comprises an amount of uniformity in at least a portion of the first and second reconstructed images.

20. The apparatus as claimed in claim 12, wherein the processing circuitry is further configured to:
scan the slab with an X-ray tube located at known locations on an X-ray scanner system, wherein the slab has a known linear attenuation coefficient and a known pathlength;
generating material decomposition data based on the scanning of the slab;
generate air calibration data based on an air scan using the X-ray tube at a rotation speed; and
calibrate the forward model for the X-ray scanner system based at least on the material decomposition data and the air scan.

* * * * *